(12) United States Patent
Lindenmann et al.

(10) Patent No.: US 11,644,053 B2
(45) Date of Patent: May 9, 2023

(54) INSTRUMENT COUPLING INTERFACES AND RELATED METHODS

(71) Applicant: Medos International Sarl, Le Locle (CH)

(72) Inventors: Philippe Lindenmann, Basel (CH); Felix Aschmann, Basel (CH); Rainer Ponzer, Oberdorf (CH); Daniela Wehrli, Wangen bei Olten (CH)

(73) Assignee: MEDOS INTERNATIONAL SARL, Le Locle (CH)

( * ) Notice: Subject to any disclaimer, the term of this patent is extended or adjusted under 35 U.S.C. 154(b) by 327 days.

(21) Appl. No.: 16/696,126

(22) Filed: Nov. 26, 2019

(65) Prior Publication Data

US 2021/0156409 A1 May 27, 2021

(51) Int. Cl.
*F16B 7/18* (2006.01)
(52) U.S. Cl.
CPC ..................................... *F16B 7/18* (2013.01)
(58) Field of Classification Search
CPC .......... F16B 2/065; F16B 5/0088; F16B 5/02; F16B 5/025; F16B 7/18; Y10T 403/1616; Y10T 403/1624; Y10T 403/5741; Y10T 403/5793; Y10T 403/589; Y10T 403/645; Y10T 403/7045; Y10T 403/7069; Y10T 403/7092; A61B 2017/0047
USPC ........... 403/13, 14, 306, 314, 320, 337, 364, 403/374.4, 380, 12
See application file for complete search history.

(56) References Cited

U.S. PATENT DOCUMENTS

| | | | |
|---|---|---|---|
| 1,918,441 A * | 7/1933 | Alsaker | F16B 2/065 411/389 |
| 5,678,944 A * | 10/1997 | Slocum | G12B 5/00 403/291 |
| 5,993,101 A | 11/1999 | Kohno et al. | |
| 6,190,395 B1 | 2/2001 | Williams | |
| 6,434,507 B1 | 8/2002 | Clayton et al. | |
| 6,556,857 B1 | 4/2003 | Estes et al. | |

(Continued)

FOREIGN PATENT DOCUMENTS

| | | | | |
|---|---|---|---|---|
| CA | 3011584 A1 * | 1/2019 | | F16B 2/065 |
| EP | 1588672 A1 | 10/2005 | | |

(Continued)

OTHER PUBLICATIONS

U.S. Appl. No. 15/820,485, filed Nov. 22 2017, Instrument Coupling Interfaces and Related Methods.

(Continued)

*Primary Examiner* — Amber R Anderson
*Assistant Examiner* — Zachary A Hall
(74) *Attorney, Agent, or Firm* — Barnes & Thornburg LLP

(57) ABSTRACT

Couplings disclosed herein can include a first coupling component having a cylindrical surface with a screw and a pin extending therefrom and a second coupling component having a prismatic surface with a first and a second through-hole. The first coupling component and the second coupling component can be configured such that relative motion between the first coupling component and the second coupling component can be restricted in all six degrees of freedom when the screw is engaged with the first through-hole to secure the cylindrical surface of the first component against the prismatic surface of the second component.

30 Claims, 23 Drawing Sheets

(56) References Cited

U.S. PATENT DOCUMENTS

| | | |
|---|---|---|
| 6,746,172 B2 | 6/2004 | Culpepper |
| 6,776,551 B2* | 8/2004 | Linnenbuerger ..... G02B 6/4219 |
| | | 24/19 |
| 6,932,823 B2 | 8/2005 | Grimm et al. |
| 7,043,961 B2 | 5/2006 | Pandey et al. |
| 7,153,297 B2 | 12/2006 | Peterson |
| 7,153,308 B2 | 12/2006 | Peterson |
| 7,166,114 B2 | 1/2007 | Moctezuma De La Barrera et al. |
| 7,274,958 B2 | 9/2007 | Jutras et al. |
| 7,289,227 B2 | 10/2007 | Smetak et al. |
| 7,314,048 B2 | 1/2008 | Couture et al. |
| 7,458,977 B2 | 12/2008 | McGinley et al. |
| 7,559,265 B2 | 7/2009 | Mizuno |
| 7,634,306 B2 | 12/2009 | Sarin et al. |
| 7,668,584 B2 | 2/2010 | Jansen |
| 7,688,998 B2 | 3/2010 | Tuma et al. |
| 7,840,256 B2 | 11/2010 | Lakin et al. |
| 7,862,568 B2 | 1/2011 | Vilsmeier et al. |
| 7,873,400 B2 | 1/2011 | Moctezuma De La Barrera et al. |
| 7,877,890 B2 | 2/2011 | Weber |
| 7,993,353 B2 | 8/2011 | Roßner et al. |
| 8,216,211 B2 | 7/2012 | Mathis et al. |
| 8,271,066 B2 | 9/2012 | Sarin et al. |
| 8,303,596 B2 | 11/2012 | Plaßky et al. |
| 8,386,022 B2 | 2/2013 | Jutras et al. |
| 8,419,750 B2 | 4/2013 | Kienzle, III et al. |
| 8,509,878 B2 | 8/2013 | Pfeifer et al. |
| 8,560,047 B2 | 10/2013 | Haider et al. |
| 8,619,504 B2* | 12/2013 | Wyssbrod ............. G04B 29/04 |
| | | 368/76 |
| 8,663,204 B2 | 3/2014 | Lechner et al. |
| 8,688,196 B2 | 4/2014 | Whitmore, III et al. |
| 8,715,296 B2 | 5/2014 | Plaßky et al. |
| 8,734,432 B2 | 5/2014 | Tuma et al. |
| 8,800,939 B2 | 8/2014 | Karsak et al. |
| 8,821,511 B2 | 9/2014 | von Jako et al. |
| 8,834,455 B2 | 9/2014 | Kleven |
| 8,961,500 B2 | 2/2015 | Dicorleto et al. |
| 8,961,536 B2 | 2/2015 | Nikou et al. |
| RE45,484 E | 4/2015 | Foley et al. |
| 9,005,211 B2 | 4/2015 | Brundobler et al. |
| RE45,509 E | 5/2015 | Foley et al. |
| 9,079,010 B2 | 7/2015 | Aho et al. |
| 9,179,984 B2 | 11/2015 | Teichman et al. |
| 9,232,985 B2 | 1/2016 | Jacobsen et al. |
| 9,265,589 B2 | 2/2016 | Hartmann et al. |
| 9,303,667 B2 | 4/2016 | Morris et al. |
| 9,393,039 B2 | 7/2016 | Lechner et al. |
| 9,498,290 B2 | 11/2016 | Piferi et al. |
| 9,539,060 B2 | 1/2017 | Lightcap et al. |
| 9,541,113 B2 | 1/2017 | Morris et al. |
| 9,649,160 B2 | 5/2017 | van der Walt et al. |
| 9,737,287 B2 | 8/2017 | Gifford et al. |
| 9,795,239 B1 | 10/2017 | Karasz et al. |
| 9,827,052 B2 | 11/2017 | Fowler et al. |
| 9,885,376 B1 | 2/2018 | Meyer et al. |
| 10,004,562 B2 | 6/2018 | Kostrzewski et al. |
| 10,028,789 B2 | 7/2018 | Quaid et al. |
| 10,182,671 B2 | 1/2019 | Firestone et al. |
| 10,288,097 B2 | 5/2019 | Ayuzawa et al. |
| 10,730,629 B2* | 8/2020 | Aury ................. B60N 2/01558 |
| 10,731,687 B2 | 8/2020 | Ponzer et al. |
| 2003/0086748 A1 | 5/2003 | Culpepper |
| 2003/0187351 A1* | 10/2003 | Franck ................. A61B 90/10 |
| | | 600/429 |
| 2004/0068263 A1 | 4/2004 | Chouinard et al. |
| 2004/0077940 A1 | 4/2004 | Kienzle et al. |
| 2004/0152955 A1 | 8/2004 | McGinley et al. |
| 2004/0171930 A1 | 9/2004 | Grimm et al. |
| 2004/0238714 A1* | 12/2004 | Slatter .................... F16B 2/065 |
| | | 248/534 |
| 2005/0049485 A1 | 3/2005 | Harmon et al. |
| 2005/0109855 A1 | 5/2005 | McCombs |
| 2005/0119639 A1 | 6/2005 | McCombs et al. |
| 2005/0124988 A1 | 6/2005 | Terrill-Grisoni et al. |
| 2005/0154296 A1 | 7/2005 | Lechner et al. |
| 2005/0203539 A1 | 9/2005 | Grimm et al. |
| 2006/0052691 A1 | 3/2006 | Hall et al. |
| 2006/0161059 A1 | 7/2006 | Wilson |
| 2007/0149977 A1 | 6/2007 | Heavener |
| 2007/0206989 A1* | 9/2007 | Wagner ............... E04F 11/1836 |
| | | 403/297 |
| 2007/0225725 A1 | 9/2007 | Heavener et al. |
| 2007/0287910 A1 | 12/2007 | Stallings et al. |
| 2008/0045972 A1 | 2/2008 | Wagner et al. |
| 2009/0180831 A1 | 7/2009 | Kendall |
| 2009/0306499 A1 | 12/2009 | Van Vorhis et al. |
| 2010/0160932 A1 | 6/2010 | Gschwandtner et al. |
| 2011/0263971 A1 | 10/2011 | Nikou et al. |
| 2012/0004534 A1 | 1/2012 | Pfeifer et al. |
| 2012/0016427 A1 | 1/2012 | Stindel et al. |
| 2012/0232377 A1 | 9/2012 | Nottmeier |
| 2013/0172907 A1 | 7/2013 | Harris |
| 2013/0178745 A1 | 7/2013 | Kyle, Jr. et al. |
| 2014/0257332 A1 | 9/2014 | Zastrozna |
| 2014/0276007 A1 | 9/2014 | Sela et al. |
| 2015/0093179 A1 | 4/2015 | Morris et al. |
| 2015/0167717 A1 | 6/2015 | Morris et al. |
| 2015/0175217 A1 | 6/2015 | Morris et al. |
| 2015/0182293 A1 | 7/2015 | Yang et al. |
| 2015/0265769 A1 | 9/2015 | Bratbak et al. |
| 2015/0297315 A1 | 10/2015 | Fowler et al. |
| 2015/0305817 A1 | 10/2015 | Kostrzewski |
| 2015/0375799 A1 | 12/2015 | Morris et al. |
| 2016/0015374 A1 | 1/2016 | Gifford et al. |
| 2016/0015474 A1 | 1/2016 | Dekel |
| 2016/0030129 A1 | 2/2016 | Christian et al. |
| 2017/0007353 A1 | 1/2017 | Fleig et al. |
| 2017/0130754 A1 | 5/2017 | Morrow |
| 2018/0296365 A1 | 10/2018 | Nielsen et al. |
| 2018/0344301 A1 | 12/2018 | Wehrli et al. |
| 2019/0021795 A1 | 1/2019 | Crawford et al. |
| 2019/0150901 A1 | 5/2019 | Ponzer et al. |

FOREIGN PATENT DOCUMENTS

| | | | |
|---|---|---|---|
| EP | 1574170 B1 | 4/2007 | |
| EP | 2636911 A1 * | 9/2013 | ............. F16B 19/02 |
| EP | 2793728 A1 | 10/2014 | |
| WO | WO 8803203 A2 * | 5/1988 | ............ F16B 7/0493 |
| WO | 9915097 A2 | 4/1999 | |
| WO | 2004030558 A1 | 4/2004 | |
| WO | 2012103254 A2 | 8/2012 | |
| WO | 2013115640 A1 | 8/2013 | |
| WO | 2015023853 A1 | 2/2015 | |
| WO | 2015162256 A1 | 10/2015 | |
| WO | 2016023599 A1 | 2/2016 | |
| WO | 2016134266 A1 | 8/2016 | |
| WO | 2017200446 A1 | 11/2017 | |

OTHER PUBLICATIONS

International Search Report and Written Opinion for Application No. PCT/EP2018/082229, dated Feb. 26, 2019 (16 pages).

International Search Report and Written Opinion for Application No. PCT/EP2020/083547, dated Mar. 4, 2021 (11 pages).

* cited by examiner

FIG. 29
FIG. 30
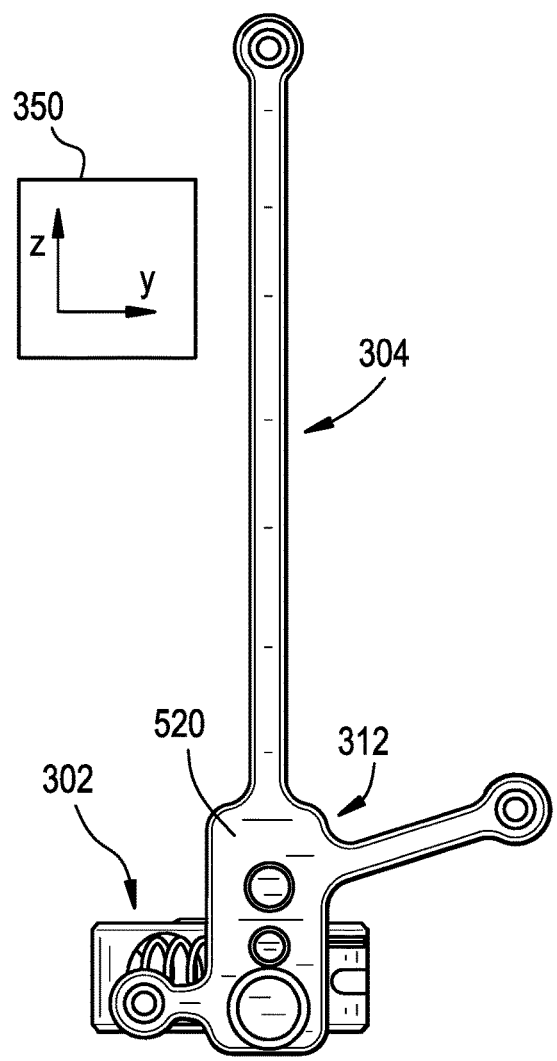
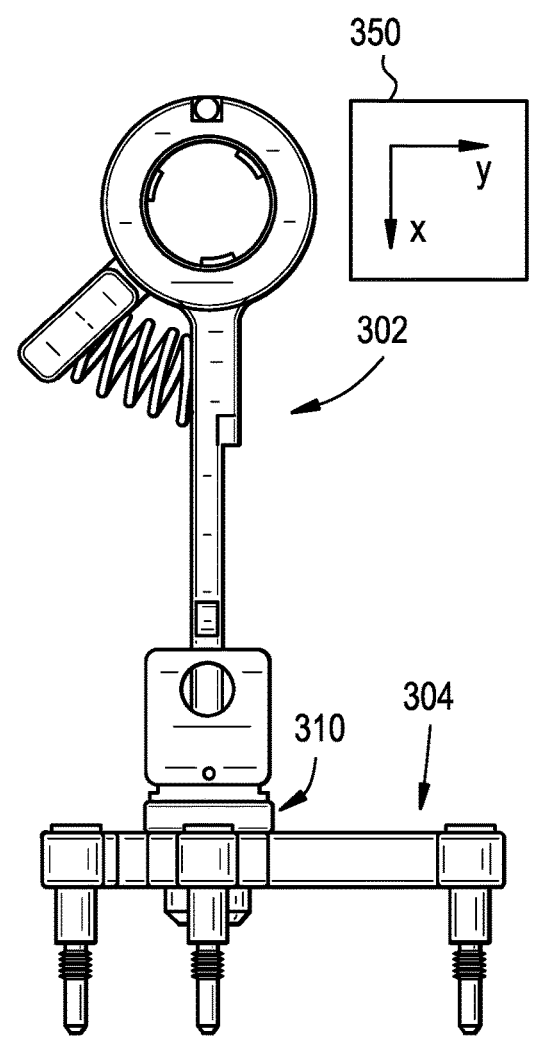

INSTRUMENT COUPLING INTERFACES AND RELATED METHODS

FIELD

Instrument coupling interfaces and related methods are disclosed herein, e.g., for coupling a surgical instrument to a navigation array or other component.

BACKGROUND

Navigation or tracking of instruments during surgical procedures has become increasingly popular. Surgical navigation can help surgeons avoid delicate neural or vascular structures when moving instruments within a patient. In spinal surgery, for example, a surgical navigation system can be used during disc removal, bone drilling, implant insertion, e.g., screw and/or cage insertion, and other steps of the surgery. Use of surgical navigation systems can also reduce the amount of X-ray exposure to which the patient and operating room staff are exposed since procedures that do not utilize surgical navigation systems typically perform more steps using fluoroscopy or other X-ray based imaging.

A typical navigation system includes an array of markers attached to a surgical instrument, an imaging system that captures images of the surgical field, and a controller that detects the markers in the captured images and tracks movement of the markers within the surgical field. The controller associates a reference frame of the imaging system with a reference frame of the patient and, informed by a known geometry of the array and the instrument, determines how the instrument is being moved relative to the patient. Based on that determination, the controller provides navigation feedback to the surgeon. The arrays can have different types or geometries, which can vary based on the navigation system, type of surgery, and/or location within the patient that is being tracked.

The precision of the navigation system strongly depends on the design of the tracked instrument and, in particular, the rigidity of the interface between the navigation array and remainder of the instrument. Welding or integrally-forming the navigation array to the instrument can result in relatively high precision being achieved. Such solutions, however, can be inconvenient, as the capability to decouple the array from the instrument or to couple the array to other instruments is absent. Further, arrangements having the navigation array integrally-formed with the instrument can require separate instruments for standard and navigation use, thereby raising costs for equipment.

A number of solutions have been developed to allow the navigation array to be interchangeably attached with one or more instruments. Such interchangeable connections can have a significant influence on precision of the instrument navigation. Interchangeable connections can include interfaces that have dovetail or v-groove geometries to connect the navigation array to the instrument. These solutions can be geometrically overdetermined, i.e., utilizing a larger number of contacting surfaces than is necessary to constrain movement of the two components. Due to manufacturing tolerances and other variations that prevent perfect mating between the many contacting surfaces in such overdetermined configurations, it can be difficult to consistently and repeatably attach the array and the instrument in a desired relative position and orientation. Other variations can be introduced into the interchangeable connection as well, for example, mechanical deformation of one or more connection interfaces that can result from interactions between components during use, etc. In the case of an overdetermined geometry, the larger number of contacting surfaces than necessary can compound the risk and effect of mechanical deformation. As a result, these solutions can allow for situations in which the navigation array can move in one or more degrees of freedom, which can undesirably reduce the precision of the navigation.

Accordingly, there is a need for improved devices, systems, and methods to securely couple a first object and a second object in a secure, precise, and repeatable relative position and orientation.

SUMMARY

Coupling assemblies are disclosed herein that can provide for a known and repeatable orientation of a first object and a second object with minimal relative movement therebetween. A coupling can include a first coupling component having a cylindrical surface with a screw and a pin extending therefrom and a second coupling component having a prismatic surface, a first opening configured to receive the screw, and a second opening configured to receive the pin. In a secured or mated configuration of the first coupling component and the second coupling component, the screw can threadably engage with the first opening and secure the cylindrical surface against the prismatic surface such that two lines of contact are formed therebetween. The pin can be received within the second opening of the second coupling component and can be configured to limit any relative movement between the first coupling component and the second coupling component that is not blocked by engagement of the screw.

In one aspect, a coupling for attaching a first object and a second object can include a first coupling component associated with the first object and a second coupling component associated with the second object. The first coupling component can have a cylindrical surface with a screw and a pin extending therefrom. The second coupling component can have a prismatic surface, a first opening configured to receive the screw, and a second opening configured to receive the pin. The first component and the second component can be adapted to mate with one another such that relative motion between the first coupling component and the second coupling component is restricted in all six degrees of freedom.

The devices and methods described herein can have a number of additional features and/or variations, all of which are within the scope of the present disclosure. In some embodiments, for example, the pin can include a proximal end, a distal end, and a reduced diameter portion located proximal to the distal end of the pin. The distal end of the pin can be a torus shape. The first coupling component and the second coupling component can be configured such that, when the first coupling component and the second coupling component are mated, at least a portion of the reduced diameter portion of the pin is disposed within the second opening of the second coupling component. In some such embodiments, the pin can be configured to limit relative movement between the first coupling component and the second coupling component along a longitudinal axis of the cylindrical surface.

The first coupling component and the second coupling component can be configured such that a clearance exists between the pin and an inner surface of the second opening when the pin of the first component is received within the second opening of the second component. In such embodiments, the distal end of the pin can contact the inner surface of the second opening to restrict movement of the second coupling component relative to the first coupling component.

In some embodiments, the first coupling component and the second coupling component can be adapted to mate with one another such that a first line of contact and a second line of contact can extend between the first coupling component and the second coupling component. The first line of contact and the second line of contact can extend between the cylindrical surface of the first coupling component and the prismatic surface of the second coupling component. Particularly, in some embodiments, the first line of contact and the second line of contact can be located on opposite sides of a midline of the cylindrical surface. The first line of contact and the second line of contact can extend along substantially an entire length of the cylindrical surface.

The prismatic surface of the second coupling component can include a first end and a second end with a first sidewall and a second sidewall extending therebetween. The first sidewall and the second sidewall can extend at an angle relative to a backstop of the prismatic surface. The first line of contact can extend along the first sidewall of the prismatic surface and the second line of contact can extend along the second sidewall of the prismatic surface.

The screw of the first coupling component can include a post having a proximal end, a distal end, and a threaded portion located proximal to the distal end of the screw. The first coupling component can further include a back surface opposite the cylindrical surface, where the back surface is a flat planar surface. In some embodiments, the first coupling component can include a through-hole configured to receive the screw such that the screw extends through the first coupling component perpendicular to the back side of the first coupling component. In some embodiments, the first object can be a surgical instrument and the second object can be a navigation array.

In another aspect, a method of coupling a first object and a second object is provided that can include aligning a first coupling component associated with the first object and a second coupling component associated with the second object. The first coupling component can have a cylindrical surface with a screw and a pin extending therefrom, and the second coupling component can have a prismatic surface, a first opening, and a second opening. The method can include advancing the first coupling component with respect to the second coupling component such that the cylindrical surface is seated against the prismatic surface, the screw is received within the first opening, and the pin is received within the second opening. The method can further include securing the first coupling component and the second coupling component in a mated configuration such that relative movement between the first coupling component and the second coupling component is restricted in six degrees of freedom.

Further, the method can include limiting relative movement between the first component and the second component by contact between the pin and an inner surface of the second opening. Securing the first component and the second component can further include driving the screw within the first opening. In some embodiments, driving the screw can prevent relative movement between the first component and the second component in at least five degrees of freedom. The method can further the pin restricting relative movement between the first component and the second component after driving the screw to secure the first component and the second component. In some such embodiments, the pin can contact an inner surface of the second opening to restrict relative movement between the first component and the second component. The restricted relative movement between the first component and the second component can be along a longitudinal axis of the cylindrical surface.

Driving the screw to mate the first component and the second component can include rotating the screw in a first direction such that a threaded portion of the screw fully engages with a threaded inner surface of the first opening. In some such embodiments, an unthreaded distal end of the screw can extend beyond a back surface of the second component when the screw fully engages with the threaded inner surface of the first opening.

In some embodiments driving the screw to mate the first component and the second component can include rotating a handle of a screw assembly in a first direction until a planar surface of the handle abuts a back surface of the first component.

The first component and the second can contact one another along a first line of contact and a second line of contact that extend between the cylindrical surface of the first component and the prismatic surface of the second component. In some such embodiments, the first line of contact and the second line of contact can be located on opposite sides of a midline of the cylindrical surface.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

FIG. 29 is a front view of the system of FIG. 3 with the first coupling component associated with the first object secured to the second coupling component associated with the second object;

FIG. 30 is a top view of the system of FIG. 3 with the first coupling component associated with the first object secured to the second coupling component associated with the second object;

DETAILED DESCRIPTION

Instrument coupling interfaces and related methods are disclosed herein, e.g., for coupling a surgical instrument to a navigation array or other component. An embodiment of a coupling of the present disclosure can include a first coupling component associated with a first object, such as a surgical instrument or a surgical instrument adapter, and a second coupling component associated with a second object, such as a navigation array. The first coupling component can be configured to mate with the second coupling component such that the first object and the second object are disposed in a known position and orientation relative to one another with minimal play or ability for relative movement. The coupling can be fully defined, i.e., can restrict movement in all six degrees of freedom, without having an overdetermined geometry that utilizes a greater number of contacting surfaces than is necessary to achieve desired movement restriction. Accordingly, the coupling can minimize or eliminate navigational inaccuracy associated with system tolerances of the objects and/or components in a navigated instrument system.

Prior Art Coupling

Figure 1:
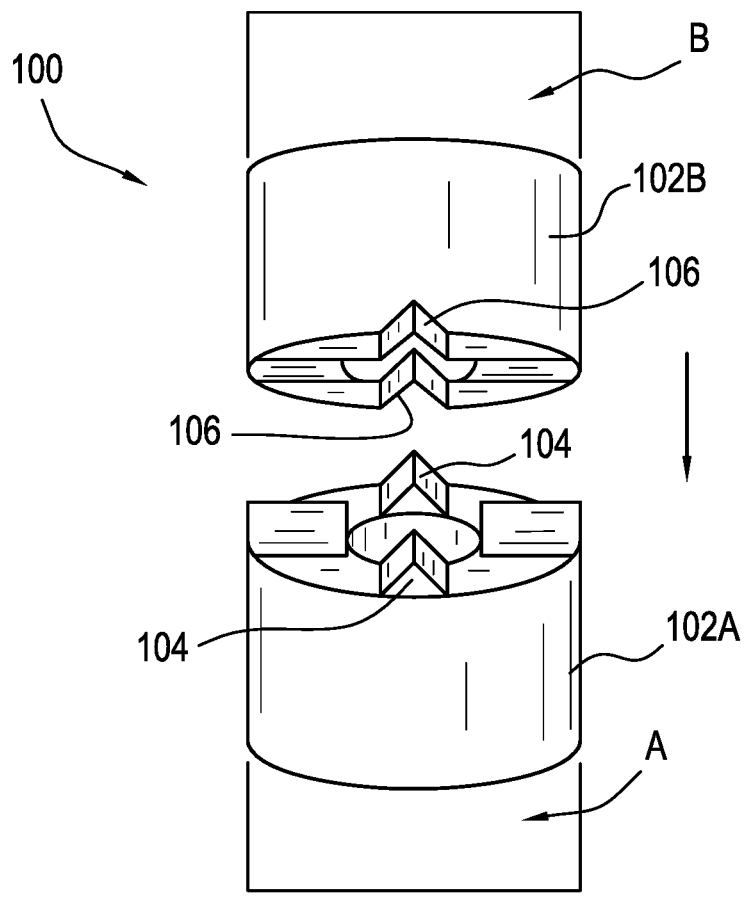
FIG. 1 is an exploded perspective view of a prior art coupling.
Figure 2:
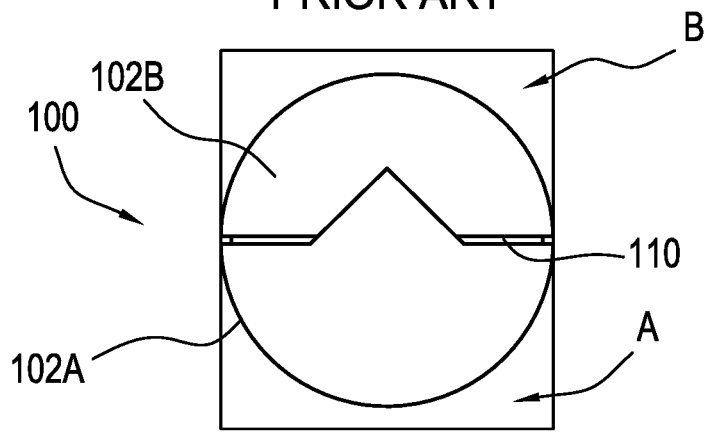
FIG. 2 is another view of the prior art coupling of FIG. 1.

FIGS. 1 and 2 illustrate a prior art coupling 100 for attaching two objects. The coupling 100 includes a first component 102A associated with a first object A and a second component 102B associated with a second object B. The first component 102A includes four V-shaped protrusions 104 that are received within four corresponding V-shaped recesses 106 of the second component 102B. The illustrated coupling 100 has an overdetermined geometry in that there are more contact points or contact surfaces than necessary to constrain the objects A, B in the desired degrees of freedom (i.e., the illustrated coupling 100 includes at least eight possible contact surfaces between the first and second components 102A, 102B). The number of protrusions and corresponding recesses may be equal to or greater than three. In such a configuration, it can be the case that not all of the eight contact surfaces may actually be in contact with each other, which can allow some degree of "play" or backlash or relative movement between the first object A and the second object B (e.g., due to a gap 110 therebetween, as shown in FIG. 2). In addition, cone or V-shaped surfaces can be very sensitive to tolerances which can lead to varying gap size when mating components are brought together. By way of further example, variation in geometry between objects or parts that are intended to have identical coupling interfaces may prevent achievement of a repeatable known position and orientation between the two mated objects. This risk is exacerbated by an over-constrained or over-determined coupling that has more points of contact than necessary. Given the constraints of such a coupling, tolerances must be tightly controlled, which can increase manufacturing cost and decrease manufacturing yield, or a certain level of inaccuracy must be accepted. Additionally, interaction between components with many small interfacing features, and/or sharp edges or surfaces, e.g., a plurality of V-shaped protrusions as shown in FIGS. 1 and 2, etc., can experience mechanical deformation or wear of one or more of the components in the coupling. Such mechanical deformation or wear can result in imperfect coupling and undesired relative movement between the components. While FIGS. 1 and 2 illustrate a coupling with V-groove geometry, dovetail and other type connections can also be overdetermined and suffer from the inaccuracies described above.

Instrument Coupling Interfaces and Related Methods

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments. The features illustrated or described in connection with one embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can be determined for different geometric shapes. Further, in the present disclosure, like-numbered components of the embodiments generally have similar features. Still further, sizes and shapes of the devices, and the components thereof, can depend at least on the anatomy of the subject in which the devices will be used, the size and shape of objects with which the devices will be used, and the methods and procedures in which the devices will be used.

Figure 3:
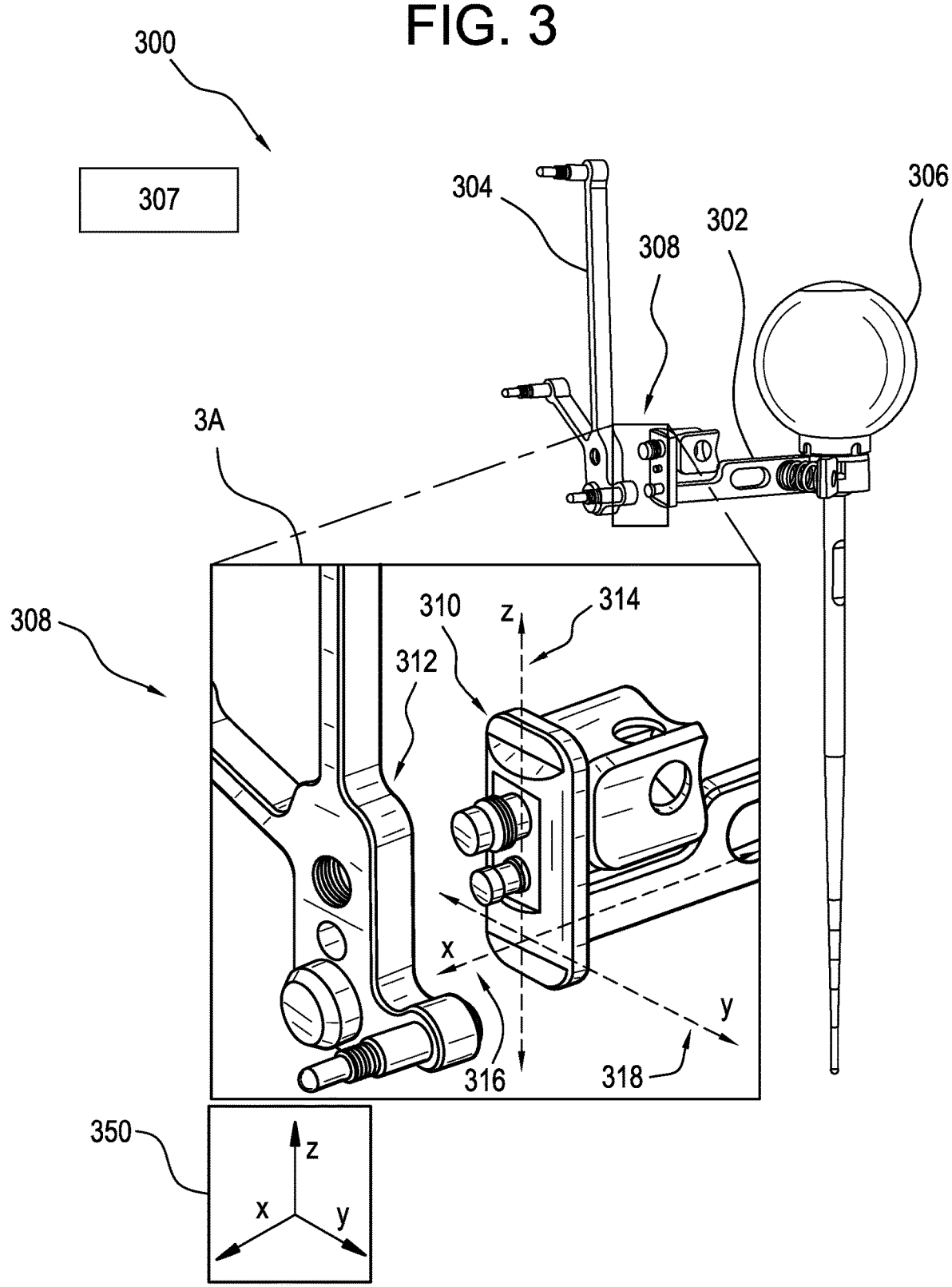
FIG. 3 shows one embodiment of a navigated instrument system including one embodiment of a coupling according to the present disclosure.

FIG. 3 illustrates one embodiment of a navigated instrument system 300 including a coupling 308 that can mate a first object (e.g., an instrument adapter 302) to a second object (e.g., a navigation array 304). The instrument adapter 302 can be configured to receive an instrument 306 therein. The navigation array 304 and the instrument 306 can be positioned within a field of view of a navigation system 307. The navigation array 304 can be detected by the navigation system 307, can communicate with the navigation system 307, or can be otherwise operably coupled to the navigation system 307 to allow the position and/or orientation of an instrument attached thereto by the coupling 308 (e.g., instrument 306 and/or instrument adapter 302) to be registered with and tracked by the navigation system. The coupling 308 can achieve consistent relative positioning of the first object and the second object with more stability than traditional couplings, and can be less prone to error introduced by system tolerances (e.g., manufacturing tolerances when creating the various components of the system). The coupling 308 can couple the navigation array 304 to the instrument adapter 302 and/or the instrument 306 in a known and repeatable position with minimal play or ability for relative movement therebetween. Accordingly, the coupling 308 can improve accuracy and reliability of navigation of the instrument 306 by more effectively coupling the two components into a single rigid construct.

The coupling 308 can be configured to provide a toggle-free, well oriented coupling with relative movement between the coupled components restricted in all six degrees of freedom. As shown in greater detail in insert box 3A, the coupling 308 can include a first coupling component 310 associated with the first object (e.g., the instrument adapter 302), and a second coupling component 312 associated with the second object (e.g., the navigation array 304). The first coupling component 310 and the second coupling component 312 can be formed integrally with the first object 302 and the second object 304, respectively. For example, a coupling component associated with a first or second object can be manufactured directly on a surface of the object itself. Alternatively, a first and/or second coupling component can be a separate component that is welded, threaded, glued, or otherwise securely associated with or attached to the first and second object, respectively.

The first coupling component 310 can be configured to mate with the second coupling component 312 to couple the first object and the second object with minimal play or ability for relative movement therebetween. The first coupling component 310 and the second coupling component 312 can be secured or mated to one another with relative movement therebetween restricted in all six degrees of freedom. As will be discussed in detail below, the coupling 308 can provide a fully defined connection between the first component 310 and the second component 312 based on a cylindrical surface of the first coupling component 310 that can be seated against a prismatic surface of the second component 312 and further secured by a screw. A pin extending from the first coupling component 310 can add stability to the coupling 308 and can further limit movement between the two components. The coupling 308 can have good durability and can mitigate the risk of mechanical deformation to the coupling components 310, 312, for example, by eliminating contact of sharp surfaces or edges and minimizing interaction between the components during coupling and decoupling.

A coordinate system will now be described with reference to the coupling 308, which will be used throughout this disclosure to aid in the description of the coupling and related methods disclosed herein. A Z-axis 314 can extend along a longitudinal axis of a cylindrical surface of the first component 310. An X-axis 316 can extend perpendicular to a back surface of the first coupling component 310. In the illustrated assembly, the X-axis can extend along a longitudinal axis of the instrument adapter 302. A Y-axis 318 can extend perpendicular to both the X-axis and the Z-axis, and transverse to the first coupling component 310 (i.e., the Y-axis can extend along a width of the first component 310, as will be described below). The coordinate system is shown in box 350, which is reproduced throughout the Figures for reference.

Figure 4:
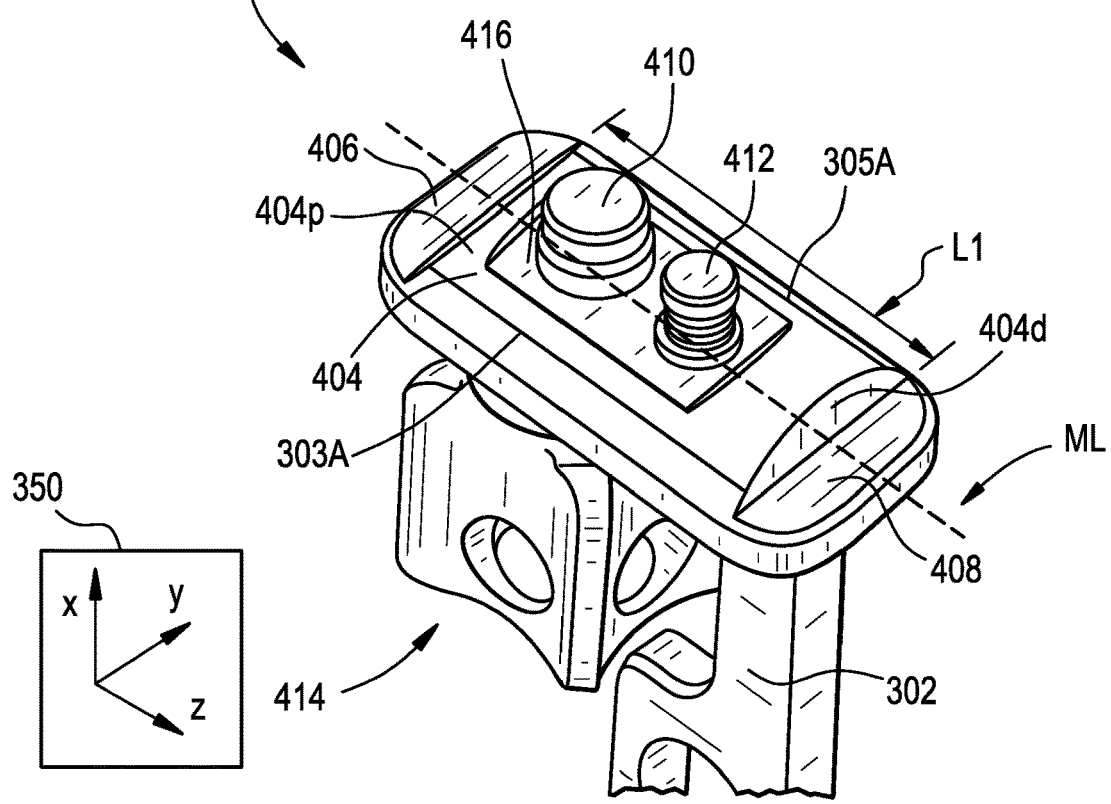
FIG. 4 is a perspective view of a first coupling component of the system shown in FIG. 3.

FIGS. 4-7 illustrate in greater detail components of the coupling 308. FIG. 4 shows the first coupling component 310 (also referred to herein as the first component). The first coupling component 310 can include a cylindrical surface 404, a screw 410, and a pin 412. The screw 410 and the pin 412 can extend from the cylindrical surface 404. The cylindrical surface 404 can have a convex profile and can extend along a substantial portion of the first coupling component 310.

In some embodiments, the first coupling component 310 can include a first end portion 406 that is proximal to a proximal end 404p of the cylindrical surface 404, and a second end portion 408 that is distal to a distal end 404d of the cylindrical surface 404. The cylindrical surface 404 can extend a length L1 between the first end portion 406 and the second end portion 408. In some embodiments, the length L1 of the cylindrical surface 404 can extend a substantial portion of a length of the first coupling component 310. The first end portion 406 and the second end portion 408 can have planar surfaces. In some embodiments, the end portions 406, 408 can ease manufacturing of the first component 310. For example, the first coupling component 310 can have chamfered edges, which can be manufactured more easily from a planar surface (i.e., the planar surface of the first and second end portions 406, 408) than a curved surface. The end portions 406, 408 can correspond to geometry of the second coupling component 312 to help align the first coupling component 310 with the second coupling component 312.

As will be described in detail below, the cylindrical surface 404 can be configured such that two lines of contact can extend between the cylindrical surface 404 and the second coupling component 312 when the first coupling component 310 is secured to the second coupling component 312. The two lines of contact can each be continuous lines. In some embodiments, each line of contact can extend along the entire length L1 or substantially the entire length L1 of the cylindrical surface 404. For example, when the first component 310 is secured to the second component 312, a first line of contact 303A can extend along a left-side of the cylindrical surface 404 (relative to a mid-line ML of the cylindrical surface extending along the Z-axis), when viewed from the perspective of FIG. 4. A second line of contact 305A can extend along a right-side of the cylindrical surface 404 (relative to the mid-line ML of the cylindrical surface), when viewed from the perspective of FIG. 4.

A screw 410 and a pin 412 can extend from the cylindrical surface 404 of the first coupling component 310. More particularly, the screw 410 and the pin 412 can extend from the cylindrical surface 404 along the X-axis of the first component 310. In some embodiments, the screw 410 and the pin 412 can be centered with respect to the mid-line ML of the cylindrical surface 404. The screw 410 and the pin 412 can be configured to be received within corresponding openings in the second component 312. In some embodiments, the screw 410 and the pin 412 can extend from a planar surface 416 that can be formed or inlayed in the cylindrical surface 404. In other embodiments, one or both of the screw 410 and the pin 412 can extend from a convex portion of the cylindrical surface 404. While the illustrated embodiment shows the screw 410 placed proximally of the pin 412 (i.e., closer to the proximal end 404*p* of the cylindrical surface), alternative configurations are within the scope of this disclosure. For example, in some embodiments, the pin 412 can be placed proximally of the screw 410.

The screw 410 can be part of a screw assembly 414, with the screw 410 disposed in a through-hole of the first component 310. As shown in FIG. 4, only a distal end of the pin 410 extends through the through-hole opening of the first component 310. This can indicate that the screw assembly 414 is not yet fully tightened with respect to the first component 310. By way of comparison, the first component 310 shown in FIG. 3 illustrates the screw assembly 414 in a tightened configuration with respect to the first component. The pin 412 can be formed integrally with the first component 310. In other embodiments, the pin 412 can be a separate component that can be welded, threaded, glued, or otherwise associated with or attached to the first component 310 such that the pin 412 extends along the X-axis of the first component.

Figure 5:
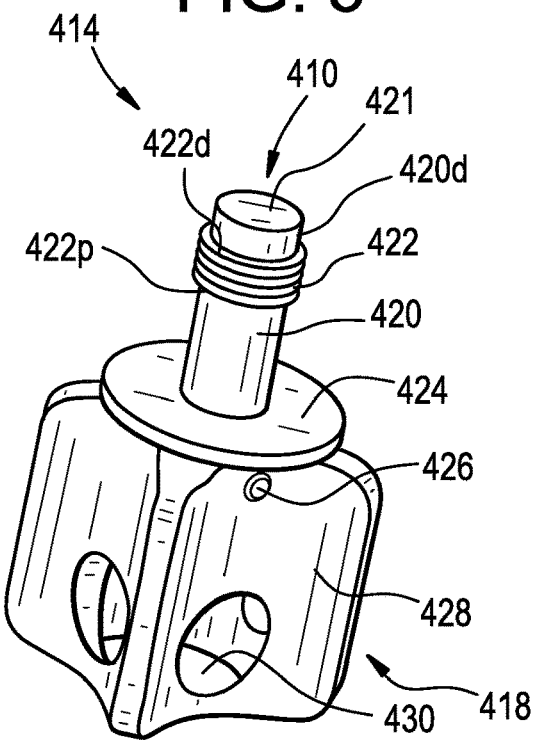
FIG. 5 is a perspective view of a screw assembly of the first coupling component shown in FIG. 4.

FIG. 5 shows the screw assembly 414 of the first component 310. The screw assembly 414 can include the screw 410 and a handle 418. The screw 410 can include a post 420 with a threaded portion 422. The threaded portion 422 can have threads that correspond to a threaded inner surface of an opening of the second component 312. In some embodiments, the threaded portion 422 can extend from a proximal end 422*p* to a distal end 422*d*. The distal end 422*d* of the threaded portion 422 can be located proximal to a distal end 420*d* of the post 420. In other words, the distal end 420*d* of the post 420 can be unthreaded and, in some embodiments, can take the form of an unthreaded cylinder. A distal surface 421 of the screw 410 can be a planar surface. The unthreaded distal end 420*d* of the screw 410 can help with alignment and can facilitate assembly of the screw 410 with a corresponding opening in the second component 312 (e.g., the unthreaded distal portion 420*d* can help align the screw prior to the threads interfacing to prevent cross-threading due to misalignment). The screw post 420 can extend from a planar outer surface 424 of the handle 418. As will be described in detail below, the planar surface 424 can be configured to abut a planar back surface of the first component 310. In some embodiments, the screw 410 can be formed integrally with the handle 418. In other embodiments, the screw 410 and the handle 418 can be separate pieces that can be securely attached to one another. For example, an assembly pin 426 can be used to attach the screw 410 to the handle 418.

One or more winged portions 428 can be formed on the handle 418. The winged portion(s) 428 can facilitate easy and secure gripping of the handle 418, e.g., for rotation of the screw 410 by a user. One or more openings 430 can be formed in the handle 418. In some embodiments, an instrument can be inserted through the one or more of the opening(s) 430 and can provide increased torque to aid in the rotation of the handle, i.e., for tightening or releasing of the screw 410. For example, a rod (not shown) can be inserted through opposing openings 430 to provide a greater lever arm, and thereby increase the torque a user can apply to the handle 418.

Figure 6:
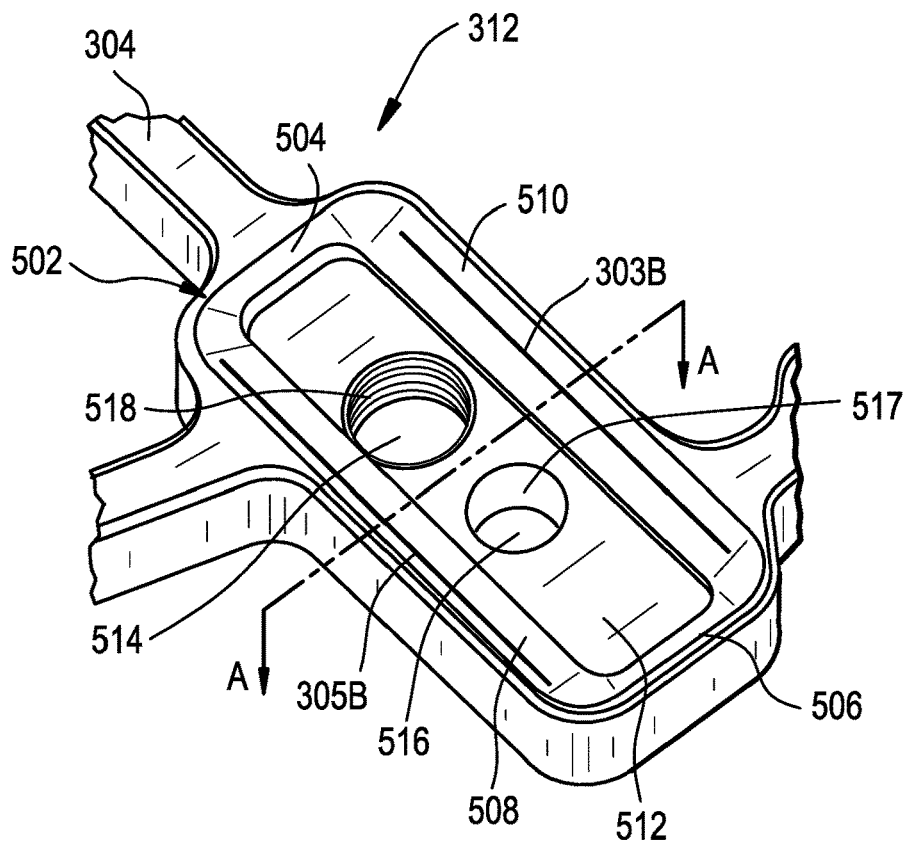
FIG. 6 is a perspective view of a second coupling component of the system shown in FIG. 3.
Figure 7:
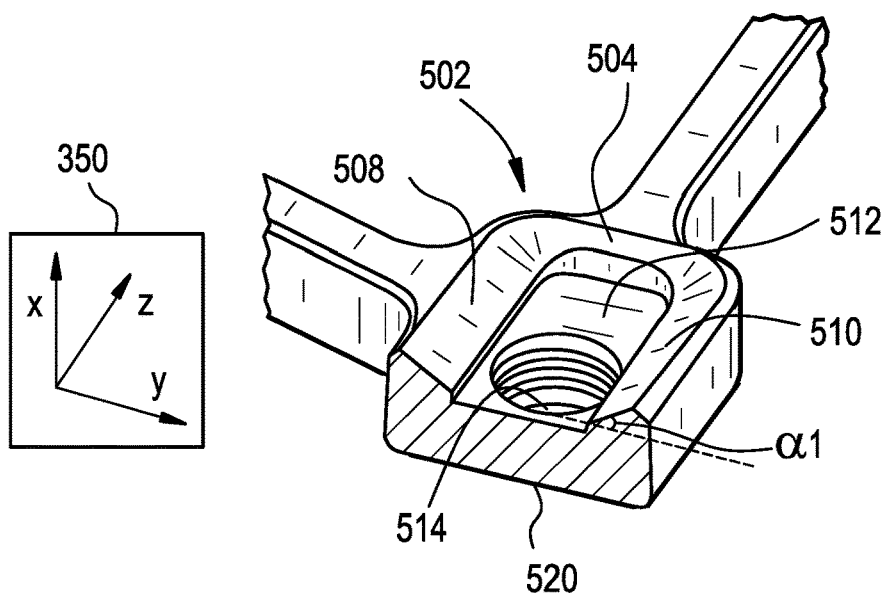
FIG. 7 is a perspective view of a cross-section of the second coupling component of FIG. 6 taken along the line A-A in FIG. 6.

FIGS. 6 and 7 illustrate the second coupling component 312 in greater detail. FIG. 6 shows a perspective view of the second coupling component 312 (also referred to herein as the second component). The second coupling component 312 can have a prismatic surface 502 with a first end 504, a second end 506, and opposing first and second sides 508, 510 extending therebetween. In some embodiments, a planar surface 512 can form a backstop to the prismatic surface 502. The planar surface 512 can ease manufacturing of the second component 312 and prismatic surface 502.

The prismatic surface 502 can be configured such that the cylindrical surface 404 of the first component 310 can be received within a recess defined by the prismatic surface 502. As discussed above, in a secured or mated configuration of the first and second components 310, 312, two lines of contact can extend between the cylindrical surface 404 and the second coupling component 312. More particularly, two lines of contact can extend between the prismatic surface 502 of the second coupling component 312 and the cylindrical surface 404 of the first coupling component 310. For example, when the first component 310 is mated with the second component 312, a first line of contact 303B can extend along the second side 510 of the prismatic surface 502, which can correspond to the first line of contact 303A that can extend along the cylindrical surface 404. A second line of contact 305B can extend along the first side 508 of the prismatic surface 502, which can correspond to the second line of contact 305A that can extend along the cylindrical surface 404. In some embodiments, the first line of contact 303B and the second line of contact 305B can extend along an entire length or substantially an entire length of the second side 510 and the first side 508, respectively. The first end 504 and the second end 506 of the second component 312 can be configured to receive the first end portion 406 and the second end portion 408 of the first coupling component 310, respectively. In some embodiments, the first end 504 and the second end 506 can include chamfered corners that can complement a geometry of the first end portion 406 and the second end portion 408 of the first coupling component 310.

The second component 312 can include a first opening 514 and a second opening 516. In some embodiments, the first opening 514 and the second opening 516 can be through-holes extending through the second coupling component 312. The first opening 514 can be configured to receive the screw 410 of the first coupling component 310. Accordingly, the first opening 514 can have a threaded inner surface 518. The threads of the threaded inner surface 518 can correspond to threads of the threaded portion 422 of the screw 410. The second opening 516 can be configured to receive the pin 412 of the first coupling component 310. In some embodiments, the second opening 516 can have a smooth or unthreaded inner surface 517. A diameter of the first opening 514 can be greater than a diameter of the second opening 516, as shown in the illustrated embodiment. In other embodiments, the diameter of the first opening 514 can be equal to or smaller than the diameter of the second opening 516. The first opening 514 and the second opening 516 can be formed in the second component 312 such that they correspond to the screw 410 and the pin 412 of the first component 310, respectively. As such, in some embodiments, the first opening 514 and the second opening 516 can have different configurations, positioning, or dimensions than that of the illustrated embodiment to properly correspond to and complement the screw 410 and the pin 412.

Figure 7A:
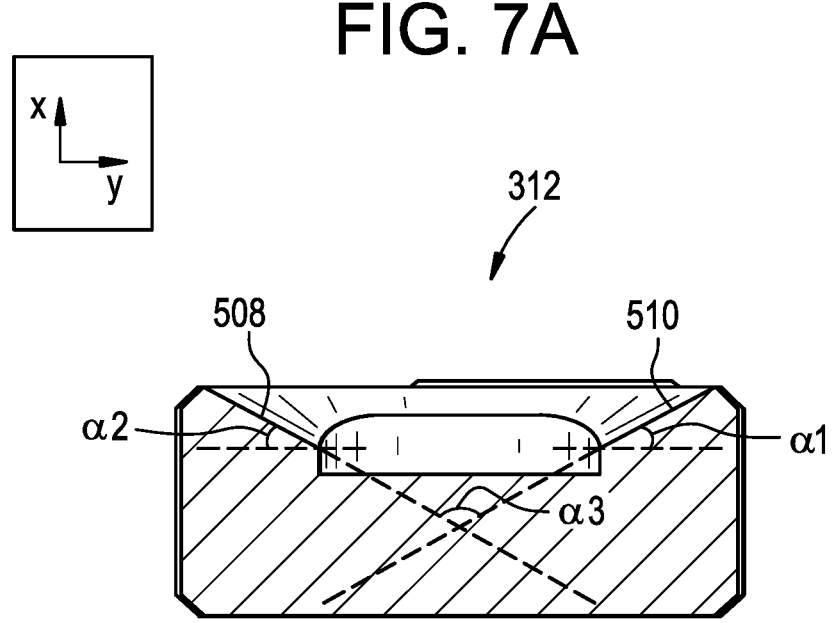
FIG. 7A is another view of the cross-section of the second coupling component of FIG. 6 taken along the line A-A in FIG. 6.

FIG. 7 shows a perspective view of a cross-section of the second component 312, taken along the line A-A of FIG. 6. A back surface 520 of the second coupling component 312 can be a planar back surface. In some embodiments, the planar back surface 520 can extend parallel to the back stop 512. FIG. 7A shows another view of the cross-section of the second component 312, taken along the line A-A of FIG. 6. As can be seen in FIG. 7A, the first side 508 and the second side 510 of the prismatic surface 502 can extend at an angle $\alpha 2$ and $\alpha 1$, respectively, relative to the Y-axis of the second component 312 (i.e., relative to an axis that extends perpendicular to a longitudinal axis of the first opening and transverse to a longitudinal axis of the prismatic surface). The angle $\alpha 2$ of the first side 508 can be the same as the angle $\alpha 1$ of the second 510. In some embodiments, however, the angle $\alpha 2$ of the first side 508 and the angle $\alpha 1$ of the second side 510 can be different. The angles $\alpha 1$, $\alpha 2$ can be selected such that the prismatic surface 502 can be configured to maintain two lines of contact with the cylindrical surface 404 of the first component 310 when the first component 310 and the second component 312 are mated. In some embodiments, the angles $\alpha 1$, $\alpha 2$ can be selected such that the first line of contact and the second line of contact between the cylindrical surface 404 and the prismatic surface 502 can be as far apart as possible for a stable coupling. By way of non-limiting example, the angles $\alpha 1$, $\alpha 2$ can each be about 30°, about 45°, or about 60°. Other angles $\alpha 1$, $\alpha 2$ of less than about 90° are also possible. In some embodiments, the angles $\alpha 1$, $\alpha 2$ can each be about 30°, which can be easier to manufacture. The angles $\alpha 1$, $\alpha 2$ can each be selected such that an angle of intersection $\alpha 3$ can be between about 30° and about 120°.

Figure 8:
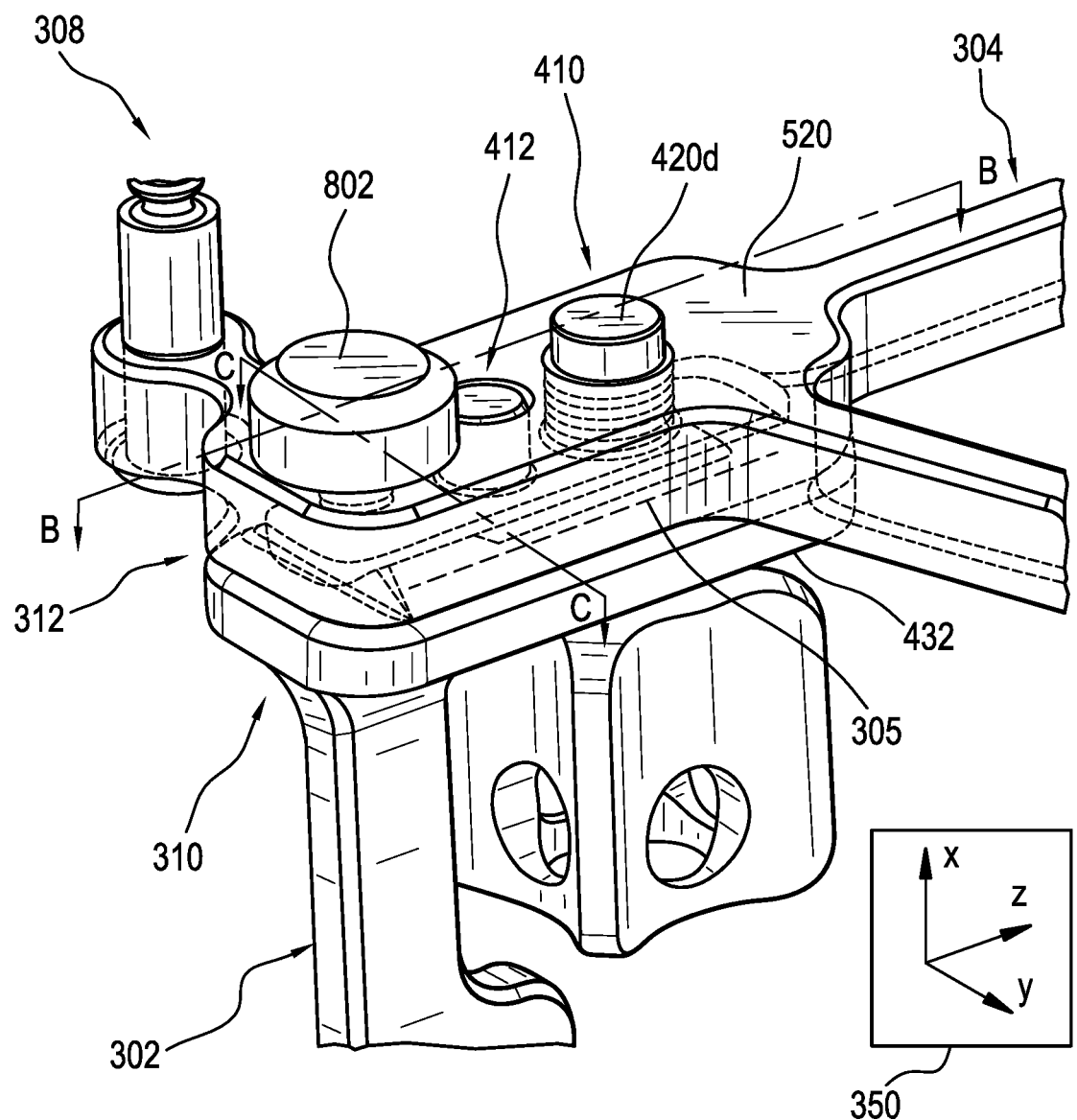
FIG. 8 is a perspective view of the first coupling component and the second coupling component of the system shown in FIG. 3 in a mated configuration.

FIG. 8 illustrates the coupling 308 in a secured or mated configuration, with the first component 310 coupled to the second component 312. In the mated configuration, the cylindrical surface 404 of the first coupling component 310 can be secured within the recess formed by the prismatic surface 502 of the second coupling component 312. The screw 410 of the first component 310 can be threadably engaged with the first opening 514 of the second component 312, and can bring the first component 310 and the second component 312 into a perfect or parallel alignment. To that end, a planar back surface 432 of the first coupling component 310 and the planar back surface 520 of the second coupling component 312 can be in parallel alignment with one another. Further, in the mated configuration, the pin 412 can be received within the second opening 516 of the second coupling component 312. As will be described in detail below, the pin 412 can limit relative movement between the first coupling component 310 and the second coupling component 312 that may exist due to, for example, frictional forces and/or tolerance variations when the first component 310 and the second component 312 are brought into alignment by the screw 410. The pin 412 can also serve to provide additional stability to the coupling 308.

Figure 9:
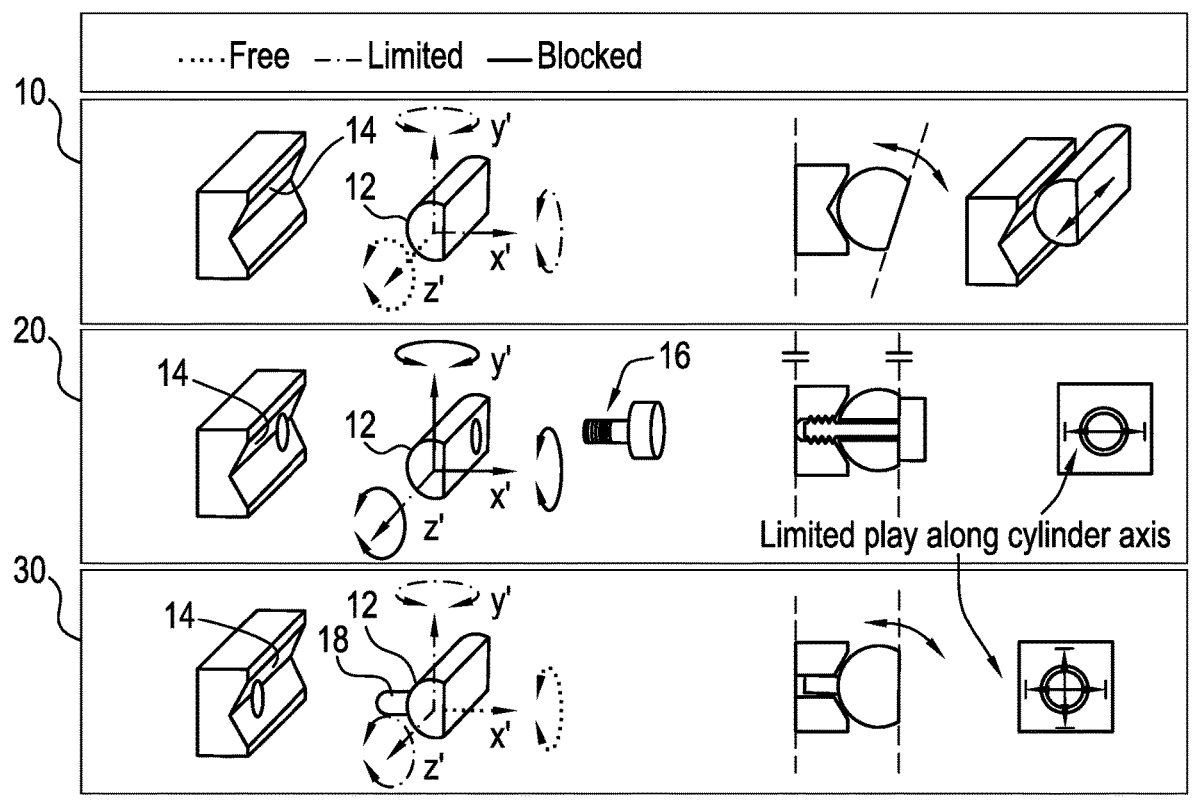
FIG. 9 is a schematic illustration of mechanical principles of a coupling according to the present disclosure.

FIG. 9 schematically illustrates the mechanical principles of the coupling 308. More particularly, FIG. 9 illustrates the ways in which various degrees of freedom can be locked or restricted by aspects of the coupling 308. A component having a cylindrical surface 12, a component having a prismatic surface 14, a screw 16, and a pin 18 of FIG. 9 can represent the first component 310 with the cylindrical surface 404, the second component 312 with the prismatic surface 502, the screw 410, and the pin 412 of the coupling 308, respectively. FIG. 9 shows a coordinate system with axes X', Y', and Z', which can be similarly defined with respect to the component having the cylindrical surface 12 as the coordinate system with axes X, Y, and, Z, as described herein with respect to coupling 308.

As illustrated in the box 10, the cylindrical surface 12 seated within a recess formed by the prismatic surface 14 can limit relative movement along, and rotation about, the X'-axis and the Y'-axis. Translation along and rotation about the Z'-axis, i.e., a longitudinal axis of the cylindrical surface 12, can remain free. The box 20 schematically illustrates the effect of the screw 16 disposed in a through-hole of the component with the cylindrical surface 12 and threadably engaged with an opening in the component having the prismatic surface 14. The screw can block relative translation along the X'-axis and the Y'-axis, and relative rotation about all three axes (X', Y', and Z'). Furthermore, the screw 16 can serve to at least limit, if not block, relative translation along the Z'-axis. In some instances, however, while relative movement along the Z'-axis can be limited by the screw 16, there may still be the potential for relative translation along the Z'-axis due to, for example, frictional forces. The pin 18 can extend from the cylindrical surface 12 and be received within an opening the component with the prismatic surface 14. As shown in the box 30, the pin 18 received within the opening can limit translation along and rotation about the Y' and Z' axes, while translation along and rotation about the X' axis are free. Accordingly, the coupling 308, as schematically illustrated in FIG. 9, can restrict relative movement in all six degrees of freedom.

Turning back to FIG. 8, the cylindrical surface 404 can be seated within the recess formed by the counterpart prismatic surface 502 and can limit relative movement along, and rotation about, the X-axis and the Y-axis. As will be described further herein, the screw 410 can threadably mate with the first opening 514 in the second component 312 to block relative movement between the first component 310 and the second component 312 in at least five degrees of freedom. The pin 412 can be received in the second opening 516 of the second component 312 and can further limit relative movement between the first component 310 and the second component 312 such that relative movement between the first component 310 and the second component 312 is blocked in all six degrees of freedom.

A line of contact 305 can extend along the Z-axis between the first component 310 and the second component 312. More particularly, the line of contact 305 can extend between the cylindrical surface 404 of the first coupling component 310 and the prismatic surface 502 of the second coupling component 312. For example, the line of contact 305 can correspond to the second line of contact 305A, 305B illustrated on the first coupling component 310 in FIG. 4 and the second component 312 in FIG. 6, respectively. While not visible in FIG. 8, an additional line of contact can extend between the first component 310 and the second component 312 on a side of the coupling 308 opposite that of the line of contact 305 (corresponding, for example, to the first line of contact 303A, 303B as indicated in FIGS. 4 and 6, respectively). It will be appreciated that the illustrated contact lines (e.g., 305, 305A, 305B, 303, 303A, 303B) are representative of contact between the first coupling component 310 and the second coupling component 312 when mated. As such, an exact placement of a line of contact can be a function of a geometry of the first coupling component 310 and the second coupling component 312, and, more particularly, can be a function of a geometry of the cylindrical surface 404 of the first coupling component 310 and the prismatic surface 502 of the second coupling component 312. Accordingly, alternative locations of one or more lines of contact than the locations as illustrated in the figures can be possible and within the scope of the present disclosure.

The coupling 308 can include an identification pin 802 that can be used as an indicator to prevent mis-assembly of the coupling 308. The identification pin 802 can be received within a corresponding opening on the back surface 520 of the second coupling component 312. The identification pin 802 can serve as a visual identifier of a lower end of the second component 312 to prevent an improper assembly of the second coupling component 312 with the first coupling component 310. Improper assembly of the coupling 308 could cause the screw 410 to be improperly aligned with the second opening 516 and the pin 412 to be improperly aligned with the first opening 514. Accordingly, the identification pin 802 can help "mistake-proof" assembly, i.e., prevent inadvertent error or mistake in the assembly of the coupling 308.

Additionally, the identification pin 802 can also serve to identify a particular characteristic of the second object 304 associated with the second coupling component 312. By way of non-limiting example, the identification pin 802 can be a color-coded pin, with a particular color identifying a particular size of the navigation array 304 (or other second object that can be associated with the second coupling component 312). In some embodiments, the entire navigation array 304 can be color-coded (e.g., coated, colored, anodized, etc.) to identify the array or a particular characteristic of the array. In this manner, a user can quickly confirm that an intended and properly sized navigation array 304 is being coupled to the first object (e.g., the instrument adapter 302) for a particular application. As can be seen in greater detail in FIG. 10, a pin receiving opening 804 can extend from the back surface 520 of the second component 312. The opening 804 can be a blind hole such that the pin 802 can be received within the second component 312 without interfering with the prismatic surface 502 of the second coupling component 312. In some embodiments, the identification pin 802 and the opening 804 can have corresponding threads that can engage to secure the identification pin 802 within the opening 804.

Figure 10:
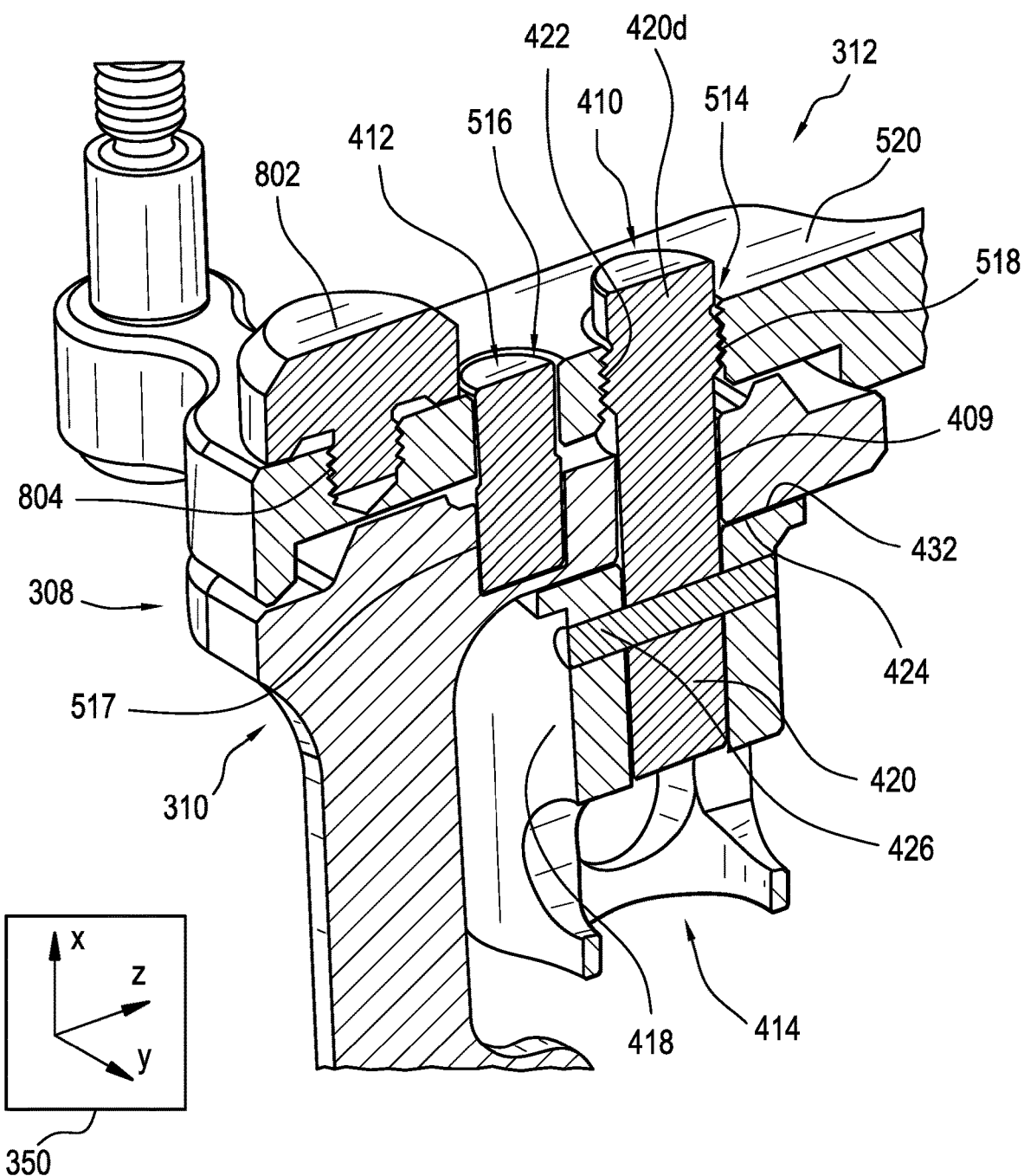
FIG. 10 is a cross-sectional view of the coupling of FIG. 8 taken along the line B-B in FIG. 8.

FIG. 10 shows a cross-sectional view of the coupling 308 in the perfect or parallel alignment, taken along the line B-B of FIG. 8. In the illustrated cross-section, the first component 310 and the second component 312 are shown mated such that the coupling 308 can constrain relative movement between the first component 310 and the second component 312 in all six degrees of freedom with minimal play. The first component 310 and the second component 312 can be brought into parallel alignment by the screw 410 engaged with the first opening 514 of the second component 312. More particularly, the threaded portion 422 of the screw 410 can be fully threadably engaged with the threaded inner surface 518 of the first opening 514 of the second component 312. In some embodiments, the first coupling component 310 and the second coupling component 312 can be fully coupled when there is full thread engagement of the threaded portion 422 of the screw 410 with the threaded inner surface 518 of the first opening 514. In such a configuration, the distal end 420d of the screw 410 can extend beyond the back surface 520 of the second component 312.

The screw 410 can extend perpendicular to the planar surface 424 of the handle 418. The assembly pin 426 can secure the screw 410 within the handle 418 to ensure a perpendicular relationship between the screw 410 and the planar surface 424. Alternatively, the screw 410 and the handle 418 can be formed in a single-piece, such that the screw assembly 414 is a unitary component. Regardless of manufacture, the screw 410 can extend perpendicularly relative to the planar surface 424 of the handle 418 such that, in the mated configuration, the screw assembly 414 can secure the first component 310 and the second component 312 in parallel alignment to one another. In some embodiments, the handle 418 can be sized for optimal engagement depth with the screw 410, and, more particularly, with the screw post 420. In other words, the handle 418 can be sized to maximize contact with the screw post 420 throughout a length of the handle 418. Optimizing the engagement between the screw post 420 and the handle 418 can reduce error in the orientation of the screw 410 relative to the handle 418.

With the screw 410 engaged with the first opening 514 to bring the first component 310 and the second component 312 into the mated configuration, the planar surface 424 of the handle 418 can align with and abut the planar back surface 432 of the first component 310. The screw 410 can be disposed in a through-hole 409 of the first component 310. A central-longitudinal axis of the through-hole 409 can be perpendicular to a planar back surface 432 of the first component 310. Accordingly, the screw assembly 414 can fix the cylindrical surface 404 of the first component 310 against the prismatic surface 502 of the second component 312. As shown in FIG. 10, engagement of the screw 410 with the first opening 514 can secure the first component 310 and the second component 312 into a parallel alignment with one another.

Threaded engagement of the screw 410 with the first opening 514 of the second component 312 can block relative movement between the first component 310 and the second component 312 in at least five degrees of freedom. The screw 410 can block relative translation along and rotation about the X-axis and Y-axis. The threadably engaged screw 410 can also block rotation between the first component 310 and the second component 312 about the Z-axis. Furthermore, the screw 410 can serve to at least limit, if not block, relative translation of the first component 310 and the second component 312 along the Z-axis. In some instances, however, while relative movement along the Z-axis can be limited by the screw 410, there may still be the potential for relative translation along the Z-axis due to, for example, frictional forces between the first component 310 and the second component 312.

The pin 412 can be received within the second opening 516 of the second coupling component 312. The pin 412 can be configured to further limit relative movement along the Z-axis, which can leave minimal play between the first coupling component 310 and the second coupling component 312. More particularly, the pin 412 and the second opening 516 can be configured such that there is only a small clearance between the pin and the inner surface 517 of the second opening 516. As such, relative movement along the Z-axis between the second component 312 and the first component 310 can be restricted to the amount that the second component 312 can move before the inner surface 517 of the second opening 516 contacts the pin 412. Similarly, the pin 412 can also serve to restrict relative movement along the Y-axis and rotation about the Y-axis and the Z-axis.

Figure 11:
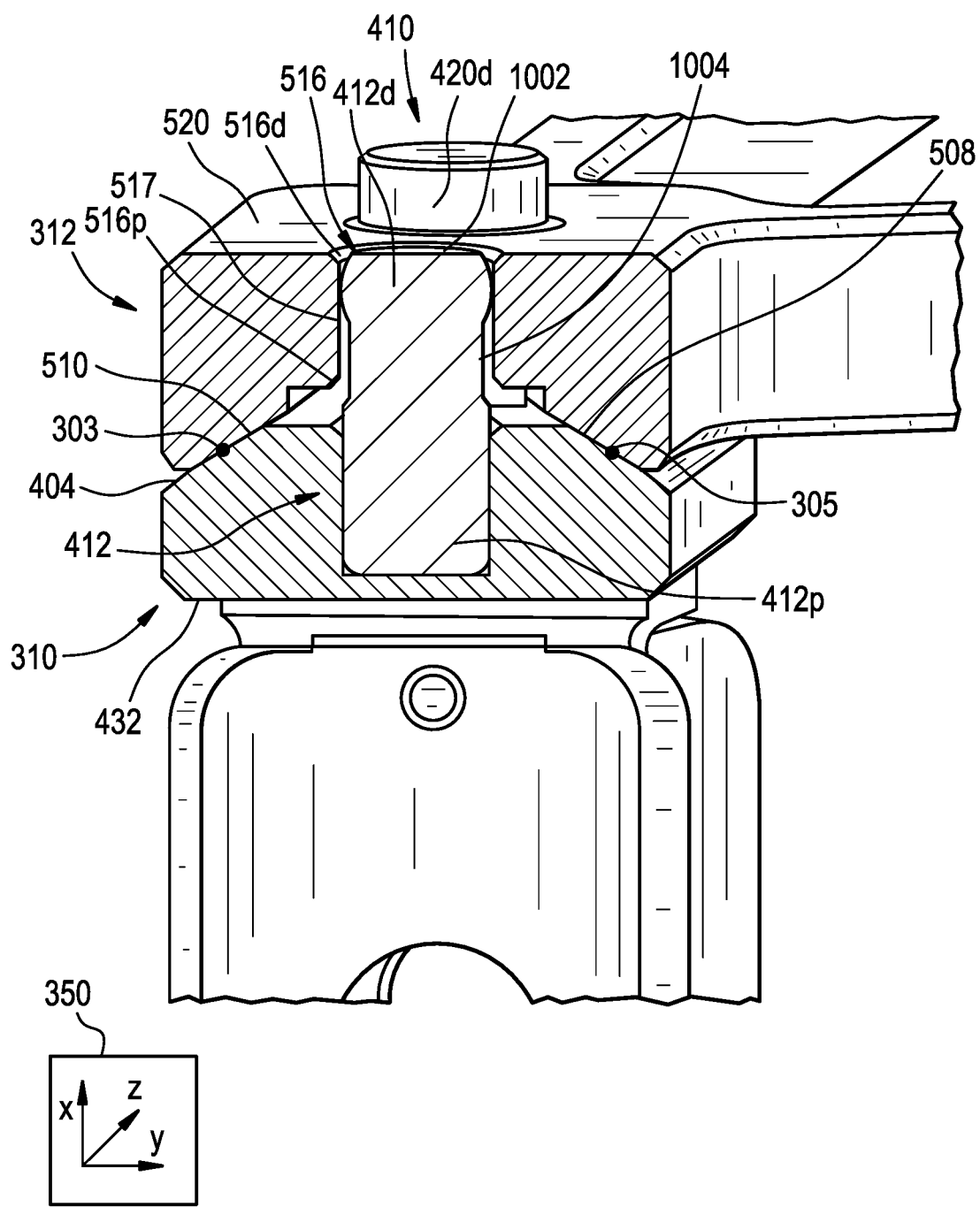
FIG. 11 is another cross-sectional view of the coupling of FIG. 8 taken along the line C-C in FIG. 8.

FIG. 11 shows a cross-sectional view of the coupling 308 taken along a line C-C of FIG. 8. In the illustrated view, the pin 412 can be seen extending perpendicularly from the first component 310. The pin 412 can be received within the second opening 516 of the second component 312 such that a distal surface 1002 of the pin 412 can be flush with the back surface 520 of the second component 312. In some embodiments, a distal end 412d of the pin 412 can have a torus shape with a planar distal surface 1002. The torus shape of the distal end 412d can allow for easier manufacturing than a distal end of another geometry, such as, for example, a sphere, though in other embodiments different distal end geometries, such as a sphere shape, etc., are possible. A proximal end 412p of the pin 412 can be seated within the first component 310 such that the pin 412 extends perpendicular to the back side 432 of the first component 310 (i.e., the pin 412 can extend from the first component 310 along the X-axis thereof). In the illustrated embodiment, the pin 412 can be a separate component that can be welded to the first component 310. As discussed above, in other embodiments the pin 412 can be threaded, glued, or otherwise securely attached to the first component 310. Alternatively, the pin 412 can be formed integrally with the first component 310.

The pin 412 can have a reduced diameter portion 1004 that can be proximal to the distal end 412d of the pin. The pin 412 can include an undercut from the distal end 412d to the reduced diameter portion 1004 such that a diameter of the reduced diameter portion 1004 is less than a diameter of the distal end 412d of the pin. Similarly, there can be an undercut from the proximal portion 412p of the pin to the reduced diameter portion 1004. As will be described in detail below, the reduced diameter portion 1004 can provide compensation for tolerance and positioning variations between the first component 310 and the second component 312, when necessary, and can guarantee that two lines of contact remain between the cylindrical surface 404 and the prismatic surface 502 despite any such variations. The reduced diameter portion 1004 can be formed such that, when the pin 412 is received within the second opening 516, the reduced diameter 1004 portion longitudinally aligns with a substantial portion of the second opening 516. More particularly, the reduced diameter portion 1004 can align with a proximal end 516p of the second opening 516 and extend longitudinally towards a distal end 516d of the second opening.

FIG. 11 shows two lines of contact between the first coupling component 310 and the second coupling component 312 in the mated configuration. The coupling 308 can be configured such that, with the first component 310 secured to the second component 312, contact between the cylindrical surface 404 of the first component 310 and the prismatic surface 502 of the second component 312 occurs only along the first and second lines of contact 303, 305. The first line of contact 303 can extend between the cylindrical surface 404 of the first component 310 and the side wall 510 of the prismatic surface 502 of the second coupling component 312. The first line of contact 303 can extend along the left side of the cylindrical surface 404, relative to the midline of the cylinder, when viewed from the perspective of FIG. 11. The second line of contact 305 can extend between the cylindrical surface 404 and the side wall 508 of the prismatic surface 502 of the second coupling component 312. The second line of contact 305 can extend along the right side of the cylindrical surface 404, relative to the midline of the cylinder, when viewed from the perspective of FIG. 11. The lines of contact 303, 305 can be spaced from one another, e.g., on opposite sides of the cylindrical surface 404 and the prismatic surface 502, and can thereby provide increased stability in the coupling 308. By way of non-limiting example, in the illustrated embodiment the cylindrical surface 404 and the prismatic surface 502 can be configured such that a distance between the first and second lines of contact 303, 305 can be about 5 mm to about 12 mm. In some embodiments, the distance between the lines of contact 303, 305 can be about 9 mm. In other embodiments, however, different distances can be possible based on the sizes of the components being joined, etc.

As discussed above, a location of the lines of contact 303, 305 can be a function of the geometry of the first coupling component 310 and the second coupling component 312. Accordingly, the lines of contact 303, 305 can fall in a different location on the cylindrical surface 404 and the prismatic surface 502 than that illustrated in the figures. For example, a cylindrical surface 404 with a smaller radius can result in the first line of contact 303 and the second line of contact 305 being located closer to a midline of the cylindrical surface 404 than those illustrated in FIG. 11. Stability of the coupling can suffer if the radius of the cylindrical surface 404 becomes too small, as any toggling or tilting of the second component 312 relative to the first component 310 could result in a drastic or disproportionate movement of the second component 312 along the cylindrical surface 404. Conversely, a cylindrical surface 404 with a larger radius can result in the first line of contact 303 and the second line of contact 305 being located farther from the midline of the cylindrical surface 404 than those illustrated in FIG. 11. If the radius of the cylindrical surface 404 becomes too large, a portion of the cylindrical surface 404 intended to be received within a recess of the prismatic surface 502 can approximate a flat surface, thereby preventing the intended coupling. An angle of the prismatic surface 502 (e.g., the angle $\alpha 1$, $\alpha 2$, and/or $\alpha 3$) can also affect the location of the first line of contact 303 and the second line of contact 305.

A geometry of a cylindrical surface 404 and/or a prismatic surface 502 can be adjusted based on factors such as, for example, application requirements and/or manufacturing constraints, so long as, in a mated configuration, a first line of contact and a second line of contact extend between the cylindrical surface 404 of the first coupling component 310 and the prismatic surface 502 of the second coupling component 312. In some embodiments, the cylindrical surface 404 and the prismatic surface 502 can be designed such that the lines of contact 303, 305 can be located as far apart as possible while maintaining a stable coupling. There can be a direct relationship between a diameter of the cylindrical surface 404 and a rotational error of the coupling 308 (i.e., rotational error can increase with an increase in the diameter of the cylindrical surface 404). As such, a diameter of the cylindrical surface 404 can be optimized in accordance with a design of the prismatic surface 502 to have an acceptable amount of rotational error for a particular usage. Additional factors that can be taken into consideration in determining a geometry of the coupling 308 can include the relationship between the angles of the prismatic surface 502 and a height of the resulting coupling 308, as well as a length of the lines of contact 303, 305 and the stability and manufacturing of the coupling 308. More particularly, increasing the angle α1, α2 of the prismatic surface 502 can result in an increased height of the coupling 308. In one embodiment, the angle α1, α2 can be about 30° which can result in a coupling 308 with an appropriate size and weight (e.g., a light weight coupling 308 that can be used for coupling a light weight navigational array to an object). A length of the lines of contact 303, 305 can contribute to the stability of the coupling 308, however, manufacturing the cylindrical surface 404 and/or the prismatic surface 502 may become more difficult as a length of the surface 404, 502 increases.

Figure 12:
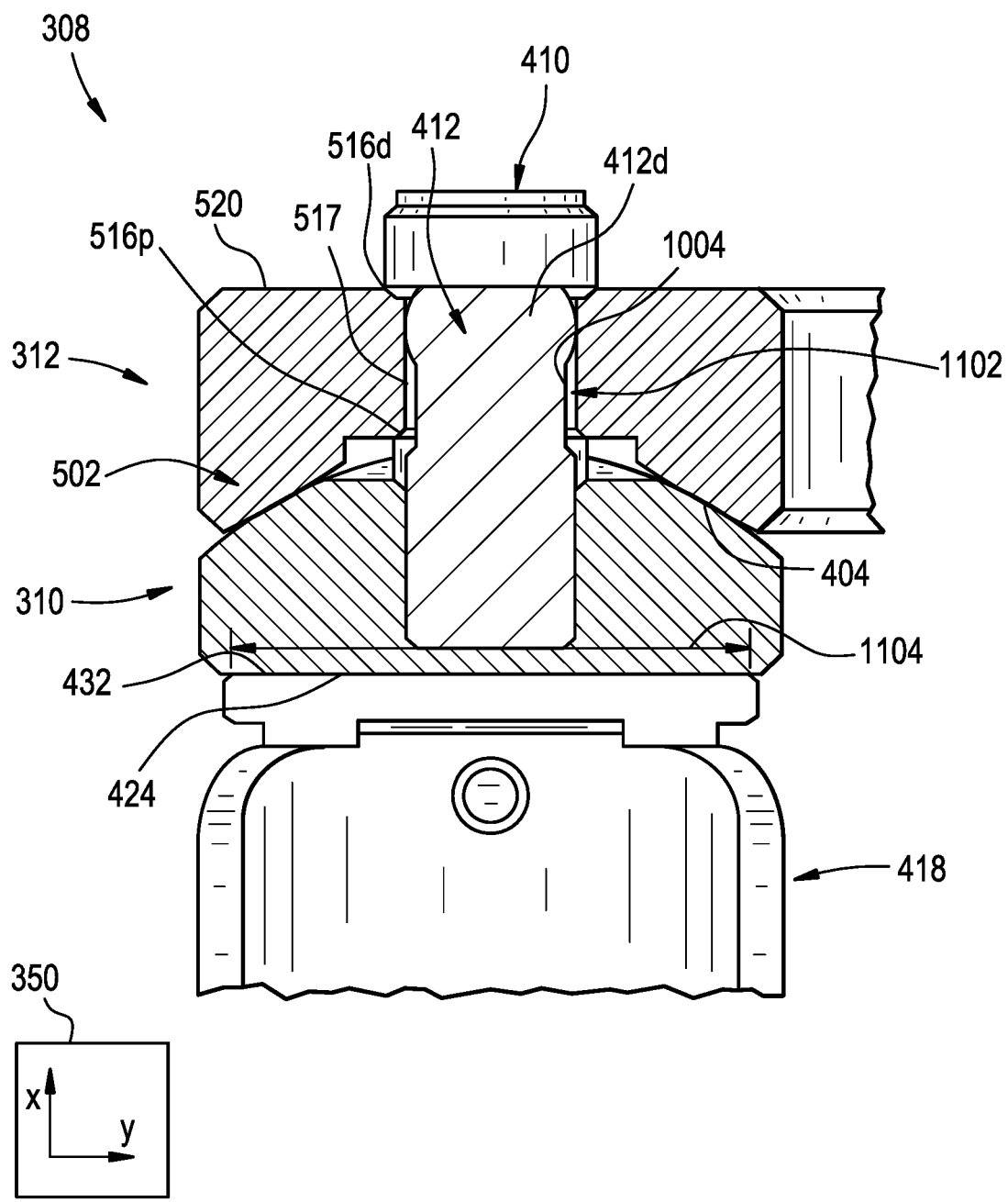
FIG. 12 is a cross-sectional view of the coupling of the system shown in FIG. 3 showing the first coupling component and the second coupling component in an ideal-alignment in a mated configuration.
Figure 13:
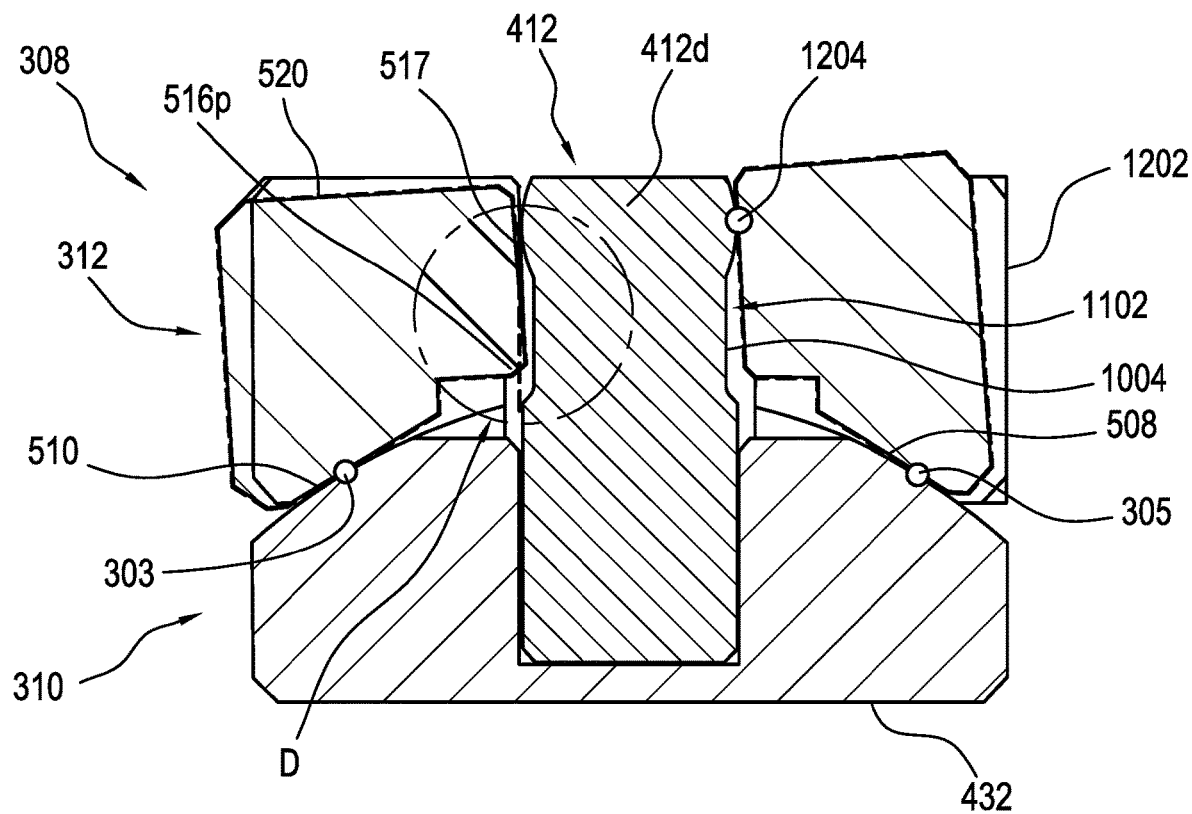
FIG. 13 is a cross-sectional view of the first coupling component and the second coupling component of the system shown in FIG. 3 in a non-parallel alignment in a mated configuration.
Figure 13A:
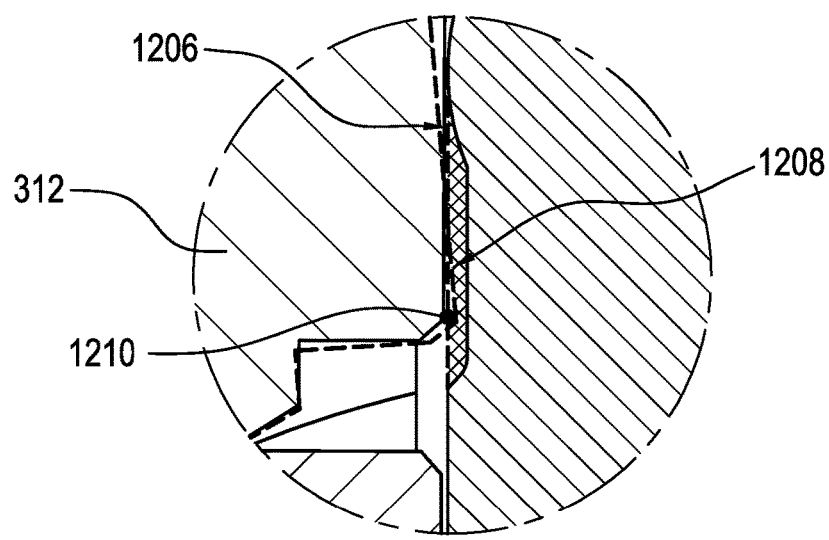
FIG. 13A is an enlarged view of the coupling shown in FIG. 13.

FIGS. 12, 13, and 13A illustrate how the pin 412 can be configured to compensate for variation in the alignment of the first component 310 and the second component 312 in the coupling 308. In some instances, the cylindrical surface 404 and the prismatic surface 502 may not be fully or perfectly aligned in the mated configuration, due to, for example, frictional forces between the components and/or tolerance variations. The pin 412 can be configured to account for and limit positional error between the two components, such that the coupling 308 can maintain a stable and reliable connection between the first component 310 and the second component 312.

As will be discussed in detail below, the pin 412 can be configured to account for tolerance-based variations in the alignment of the first component 310 and the second component 312 such that, notwithstanding these variations, two lines of contact between the cylindrical surface 404 and the prismatic surface 502 can be maintained in the coupling 308. Further, the distal end 412d of the pin 412 can provide an additional point of contact between the first component 310 and the second component 312 when the first component 310 and the second component 312 are not in a perfect alignment. The additional point of contact can limit the degree to which the second component 312 can tilt relative to the first component 310. The reduced diameter portion 1004 of the pin 412 can compensate for tolerance variations (i.e., tilting or other variation from ideal relative positioning) in the alignment of the first component 310 and the second component 312 such that a first line of contact 303 and a second line of contact 305 can be maintained in the coupling 308. Accordingly, the coupling 308 can provide precise attachment and orientation of a first object (e.g., the instrument adapter 302) associated with the first component 310 and a second object (e.g., the navigation array 304) associated with the second component 312.

FIG. 12 shows the first component 310 and the second component 312 perfectly aligned in the mated configuration of the coupling 308. In some embodiments, perfect or ideal alignment can be evidenced from the back surface 432 of the first component 310 extending parallel to the back surface 520 of the second component 312. To help achieve perfect or parallel alignment between the first and second components 310, 312, it can be beneficial to have extended contact area between the handle 418 and the first component 310. Such extended contact can provide good leverage for the handle 418 to bring the components 310, 312 into parallel alignment. For example, a diameter 1104 of a contact area between the planar surface 424 of the handle 418 and the back surface 432 of the first component 310 can extend across a width the first component 310 (i.e., across the Y-axis of the first component 310). In some embodiments, the diameter 1104 can extend across an entire or substantially an entire width of the back surface 432 of the first component 310.

A clearance 1102 can extend between the pin 412 and the inner surface 517 of the second opening 516. In the ideal parallel alignment, the clearance 1102 can extend between the pin 412 and the inner surface 517 along a full length of the second opening 516 (i.e., from the proximal end 516p to the distal end 516d of the second opening 516). The clearance 1102 can be small between the distal end 412d of the pin 412 and the inner surface 517 of the second opening 516 such that the two components can slide past one another but there is negligible play between the components. As will be discussed in detail below, the clearance 1102 can widen along the reduced diameter portion 1004 of the pin 412. In some embodiments, such as the perfectly aligned configuration of FIG. 12, the screw 410 can successfully bring the first component 310 and the second component 312 into parallel alignment and restrict movement in all six degrees of freedom without the pin 412 contacting the second component 312.

In contrast to the coupling illustrated in FIG. 12, in some instances, alignment between the first component 310 and the second component 312 can be imperfect after the screw 410 engages with the first opening 514 to secure the first and second components 310, 312. FIG. 13 shows the coupling 308 in one such instance, with the first component 310 and the second component 312 in a non-parallel alignment due to, for example, friction between the two components and/or tolerance variations. Note that the scale in these figures is exaggerated and the degree of tilting or misalignment between components can be small, e.g., so small that it does not impact the ability of threads formed on the screw 410 and the opening 514 to properly engage. As illustrated, the second component 312 can be tilted relative to the first component 310 such that the back surface 520 of the second component 312 extends at an oblique angle relative to the back surface 432 of the first component 310. An outline 1202 of a parallel- or perfectly-aligned second component 312 is shown for comparison. An additional point of contact 1204 can occur between the distal end 412d of the pin 412 and the second component 312. Accordingly, a tilting of the second component 312 can be restricted to the point at which the inner surface 517 of the second opening 516 contacts the distal end 412d of the pin 412. The point of contact 1204 can thus constrain the orientation of the second component 312 relative to the first component 310 to a known and predictable configuration, and can provide stability to the coupling 308.

As discussed above, the clearance 1102 can widen between the reduced diameter portion 1004 of the pin 412 and the inner surface 517 of the second opening 516. The clearance 1102 can allow two lines of contact 303, 305 to be maintained between the second component 312 and the first component 310 despite the non-parallel alignment of the components. More particularly, because the reduced diameter portion 1004 of the pin 412 aligns with a substantial portion of the opening 516 in the second component 312, including the proximal end 516p of the second opening 516, a portion of the sidewall of the second opening 516 can extend into the clearance 1102 in the non-parallel alignment without contacting the pin 412. Such a configuration can allow the second component 312 to maintain contact with and move along the cylindrical surface 404 of the first component 310. For example, in the orientation illustrated in FIG. 13, the two lines of contact 303, 305 can be maintained despite the tilting of the second component 312. The prismatic surface 502 (i.e., the sidewalls 508, 510) can translate along and maintain contact with the cylindrical surface 404. As such, the reduced diameter portion 1004 of the pin 412, and the resulting clearance 1102, can add stability to the coupling 308 by allowing for two lines of contact (e.g., lines of contact 303, 305) to be maintained between the first component 310 and the second component 312 despite a non-parallel or non-ideal alignment of the first and second components. Accordingly, even without parallel or ideal alignment, the coupling 308 in the secured position can limit relative motion between the first component 310 and the second component 312 in all six degrees of freedom.

With reference to FIG. 13A, which shows a portion of FIG. 13 within the area D in greater detail, an alternative pin with a straight profile 1206 (i.e., an alternative/straight pin without a reduced diameter portion) could result in a loss of contact between the first component 310 and the second component 312 in the non-parallel or non-ideal alignment. This is because the straight profile 1206 of a pin would create an area of conflict 1208 between the pin and the second component 312 when the second component 312 is tilted relative to the first component 310. This can result in a loss of at least one line of contact between the first component 310 and the second component 312 and can negatively impact the stability of the coupling 308. For example, a second point of contact 1210 can occur between the straight profile 1206 of the alternative pin and the second component 312. This contact can pivot the second component 312 away from the first component 310 and result in a loss of contact between the prismatic surface 502 and the cylindrical surface 404.

Figure 14:
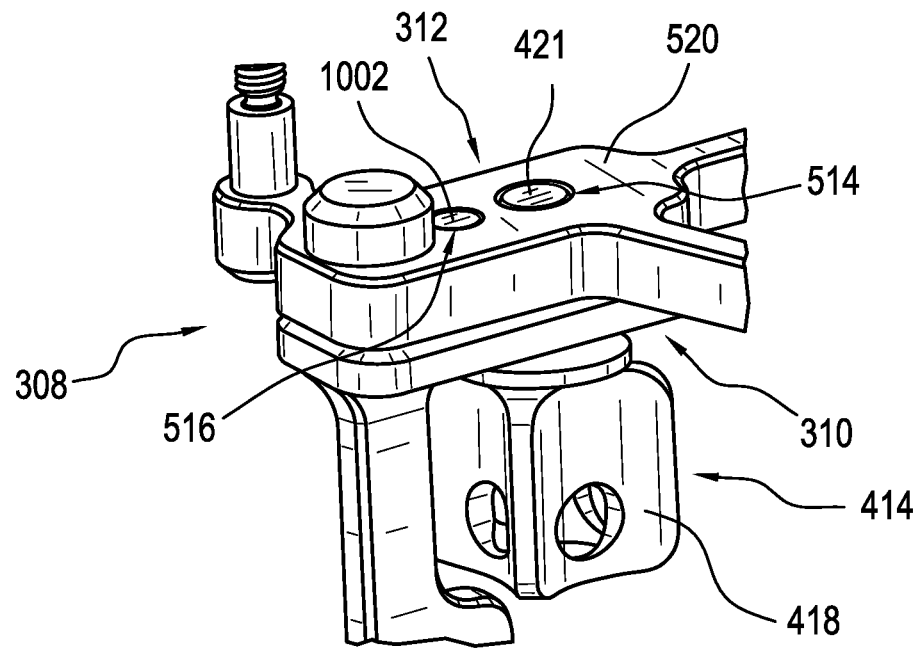
FIG. 14 is a perspective view of the coupling of the system of FIG. 3 with the first coupling component seated within the second coupling component.

FIG. 14 illustrates the coupling 308 with the first component 310 seated within the second component 312. The screw 410 and the pin 412 of the first component 310 can be received within the first and second openings 514, 516 of the second component 312, respectively. While not visible, the cylindrical surface 404 of the first coupling component 310 can be seated within a recess formed by the prismatic surface 502 of the second coupling component 312. The distal surface 1002 of the pin 412 can be flush with the back surface 520 of the second component 312. The distal surface 421 of the screw 410 can be flush with the back surface 520 of the second component 312. In some embodiments, the distal surface 421 of the screw 410 being flush with the back surface 520 of the second component 312 can indicate that the screw 410 is not threadably engaged with the opening 516. Accordingly, the first component 310 and the second component 312 can be seated, but not yet fully mated or secured. In the seated configuration, relative motion between the first component 310 and the second component 312 can be limited, but not yet blocked, in one or more degree of freedom, e.g., by one or more of the contact between the cylindrical surface 404 and the prismatic surface 502, the pin 412 received within the second opening 516 and the screw 410 received within the first opening 514.

Figure 15:
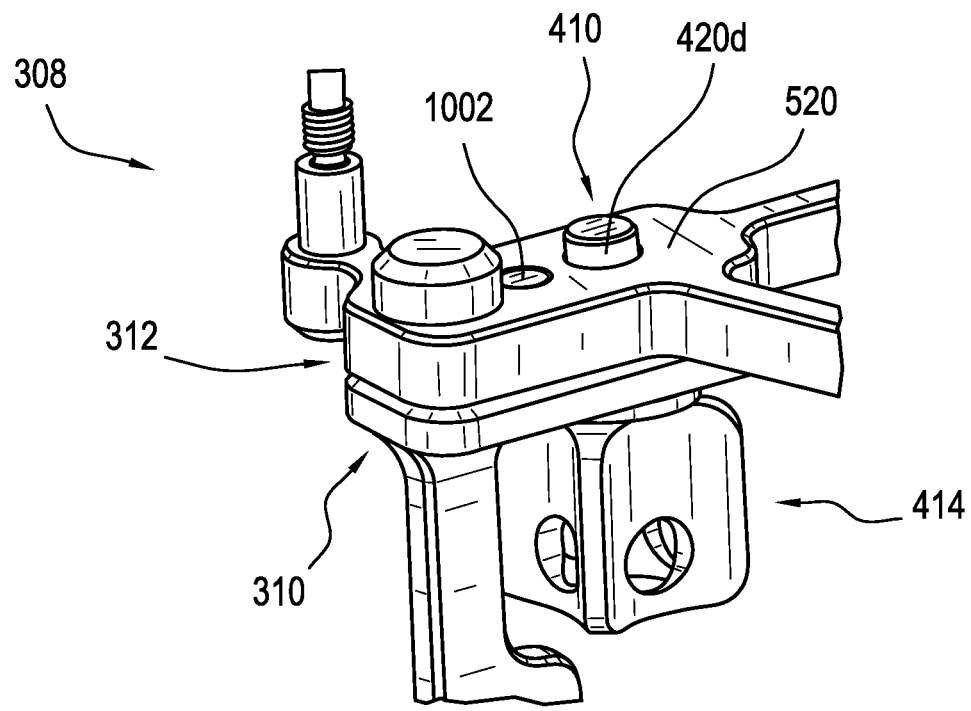
FIG. 15 is a perspective view of the coupling of the system of FIG. 3 with the first coupling component mated to the second coupling component.

FIG. 15. Illustrates the coupling 308 with the first component 310 mated with or secured to the second component 312. The screw assembly 414 can be actuated to drive the screw 410 to mate the first component 310 with the second component 312. For example, a user can rotate the handle 418 in a first direction to drive the screw 410 within the first opening 514. In some embodiments, the distal end 420d of the screw 410 can extend past the back surface 520 of the second component 312. This can indicate that the screw 410 has been driven to threadably engage with the first opening 514. In some embodiments, the entirety of the unthreaded distal end 420d of the screw 410 can protrude from the first opening 514. This can serve as a visual indication that an entire length of the threaded portion 422 of the screw 410 is engaged with the threaded inner surface 518 of the first opening 514. The distal surface 1002 of the pin 412 can remain flush with the back surface 520 of the second component 312 when the first component 310 and the second component 312 are mated. As discussed above, in such a mated configuration, the screw 410 and pin 412 can block relative movement between the first component 310 and the second component 312 in all six degrees of freedom, such that there is negligible play between the components 310, 312. In some embodiments, the first component 310 and the second component 312 can have a matching outer perimeter. Matching outer perimeters of the first and second components 310, 312 can produce a continuous and smooth profile of the coupling 308 and allow for quick visual confirmation that the components are properly aligned with one another.

To decouple the first component 310 from the second component 312, the handle 418 can be driven or rotated in a second direction such that the screw 410 disengages from the first opening 514. More particularly, as the screw 410 is rotated in the second direction, the threaded portion 422 of the screw 410 can move proximally through the opening 514 such that a proximal end 422p of the threaded portion 422 can exit the threaded surface 518 of the first opening 514. The first component 310 and the second component 312 can be completely decoupled when the distal end 422d of the threaded portion 422 exits the threaded surface 518 of the first opening 514. The first component 310 can then be moved away from the second component 312.

Generally, the first component 310 and the second component 312 can be manufactured from a hard metal, such as steel, titanium, or the like to reduce wear and allow reuse of the instruments or objects on which the components are formed or disposed. In other embodiments certain polymers or other materials may also be appropriate for use in forming the first and second components 310, 312.

The coupling 308 can be used to couple a first object associated with the first coupling component 310 to a second object associated with the second coupling component 312. The coupling 308 can be used with any of a variety of instruments or objects. For example, in some embodiments, the first object can be an instrument adapter (e.g., instrument adapter 302) configured to receive an instrument (e.g., instrument 306) therein, and the second object can be a navigation array (e.g., navigation array 304). A position and orientation of the coupling components 310, 312 with respect to the navigation array (e.g., navigation array 304) can be known, such that the position and orientation of the instrument 306 attached to the array 304 by the coupling 308 (e.g., instrument 306 placed within instrument adapter 302) can be determined from the position and orientation of the array 304. In alternative embodiments, the first object can be an instrument such that the instrument may be directly coupled to a navigation array 304 via a coupling 308 without the need for an instrument adapter 302. While reference is made herein to the instrument adapter 302 as the first object associated with the first coupling component 310 and to the navigation array 304 as the second object associated with the second coupling component 312, in other embodiments the instrument adapter 302 can be associated with the second coupling component 312 while the navigation array 304 can be associated with the first coupling component 310.

FIGS. 16-21 illustrate embodiments of the instrument adapter 302 associated with the first coupling component 310 and the navigation array 304 associated with the second coupling component 312. The first component 310 and the second component 312 can be identical to that of the first component and the second component described in detail above, with reference to FIGS. 3-15. Accordingly, a detailed description of their structure, operation, and use is omitted from the description of FIGS. 16-21 for the sake of brevity.

Figure 16:
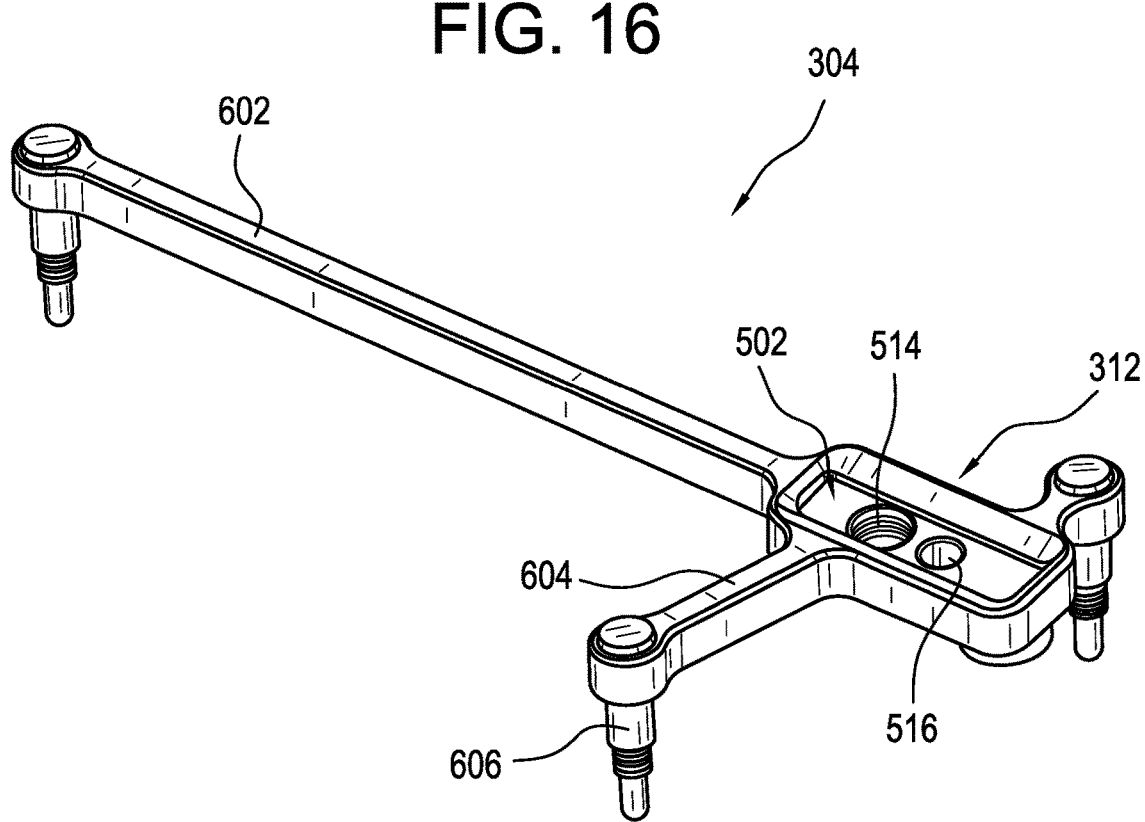
FIG. 16 is a perspective front view of the navigation array associated with the second coupling component of the system of FIG. 3.
Figure 17:
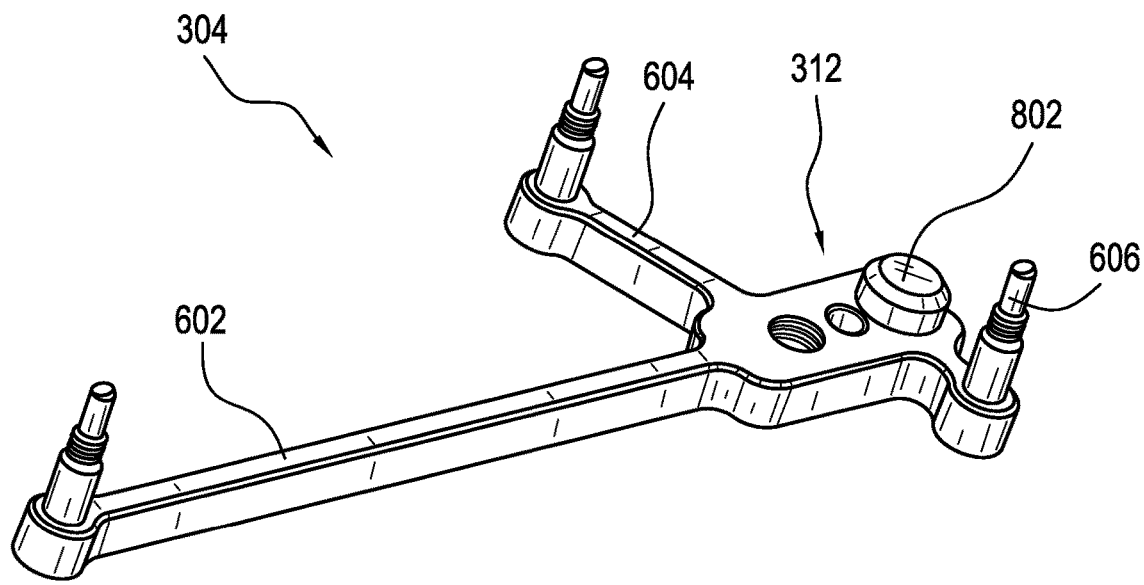
FIG. 17 is a perspective back view of the navigation array of FIG. 16.
Figure 18:
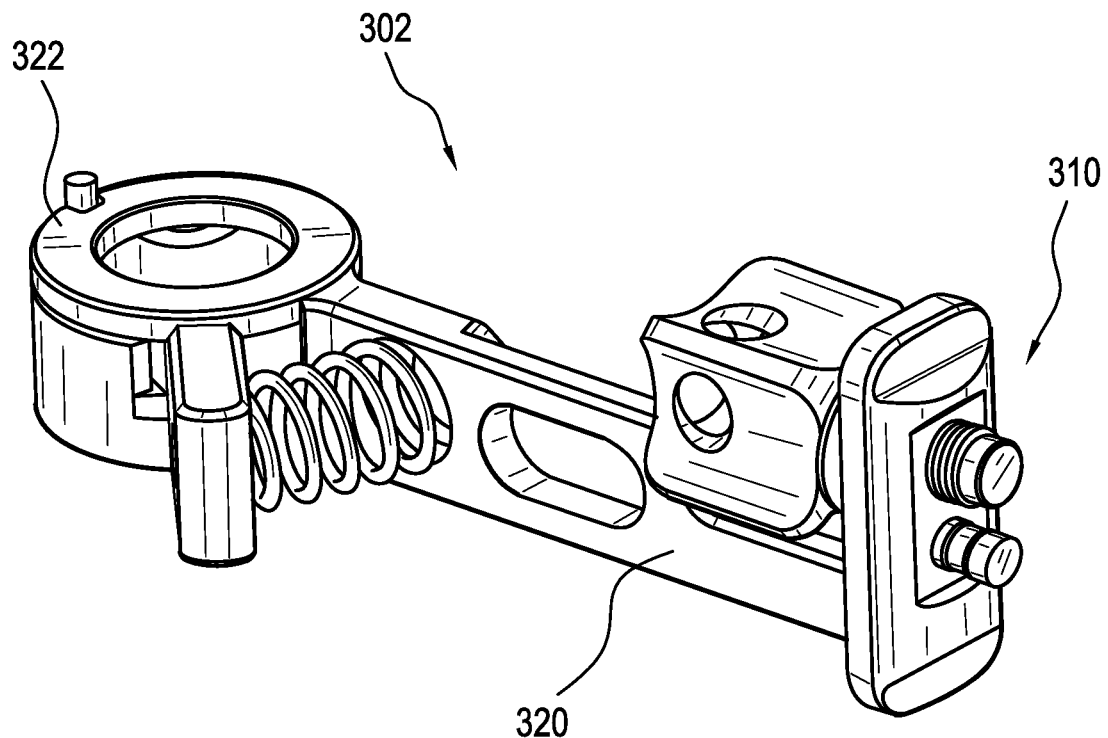
FIG. 18 is a perspective view of the instrument adapter associated with the first coupling component of the system of FIG. 3.

FIGS. 16 and 17 show an embodiment of a navigation array 304 that can be used with the coupling 308 of the present disclosure. The navigation array 304 can include a frame 602 with the second component 312 formed thereon, e.g., integrally formed in the frame 602 or attached thereto. The frame 602 can include one or more branches 604. Each branch 604 can have an attachment feature 606 that can receive a sphere-shaped fiducial or other marker for use with a navigation system. The attachment feature(s) 606 can be arranged in predetermined positions and orientations with respect to one another and/or the frame 602. The attachment features 606 can be positioned such that, in use, markers attached thereto can be placed within a field of view of a navigation system and can be identified in images captured by the navigation system. By way of non-limiting example, markers can include infrared reflectors, LEDs, and so forth. The branches 604 and/or attachment features 606 can be arranged on a navigation array 304 with different positions and/or orientations to that of the illustrated navigation array 304. For example, while the navigation array 304 illustrated in FIGS. 16 and 17 has three branches 604 with each branch having a single attachment feature 606, a navigation array 304 can have a greater or fewer number of branches and/or attachment features. The navigation array 304 can include an inertial measurement unit (IMU), an accelerometer, a gyroscope, a magnetometer, other sensors, or combinations thereof. In some embodiments, the sensors can transmit position and/or orientation information to a navigation system, e.g., to a processing unit of the navigation system.

In the navigation array 304 illustrated in FIGS. 16 and 17, a coupling component (e.g., the first or second component described above) can be disposed on a lower surface or lower portion of the array. For example, the second component 312 of the coupling 308 can be integrally formed with or attached to a lower portion of the navigation array 304. Accordingly, in some embodiments, the navigation array 304 can function as the second object to be coupled to a first object by the coupling 308. FIG. 16 shows a front side of the navigation array 304 with the second component 312 formed at the lower portion of the frame 602. In other embodiments, the second component 312 can be disposed at a different location relative to the navigation array 304. The prismatic surface 502 of the second component 312 can be formed on the front side of the navigation array 304. FIG. 17 illustrates a back side of the navigation array 304 with the second component 312 formed at the lower portion of the frame 602. As can be seen, the identification pin 802 of the second coupling component 312 can be visible on the back side of the navigation array 304.

FIGS. 18-21 show various views of an embodiment of an instrument adapter 302 associated with the first coupling component 310. The instrument adapter 302 can include an arm 320 with an instrument ring 322 at a first end thereof. Additional details about the instrument ring 322 can be found in U.S. Patent Application Publication No. 2018/0344301, filed on May 31, 2017, and entitled "Coupling Devices for Surgical Instruments and Related Methods" to Wehrli et al., which is hereby incorporated by reference in its entirety. The instrument ring 322 can be configured to securely receive an instrument therein.

Figure 19:
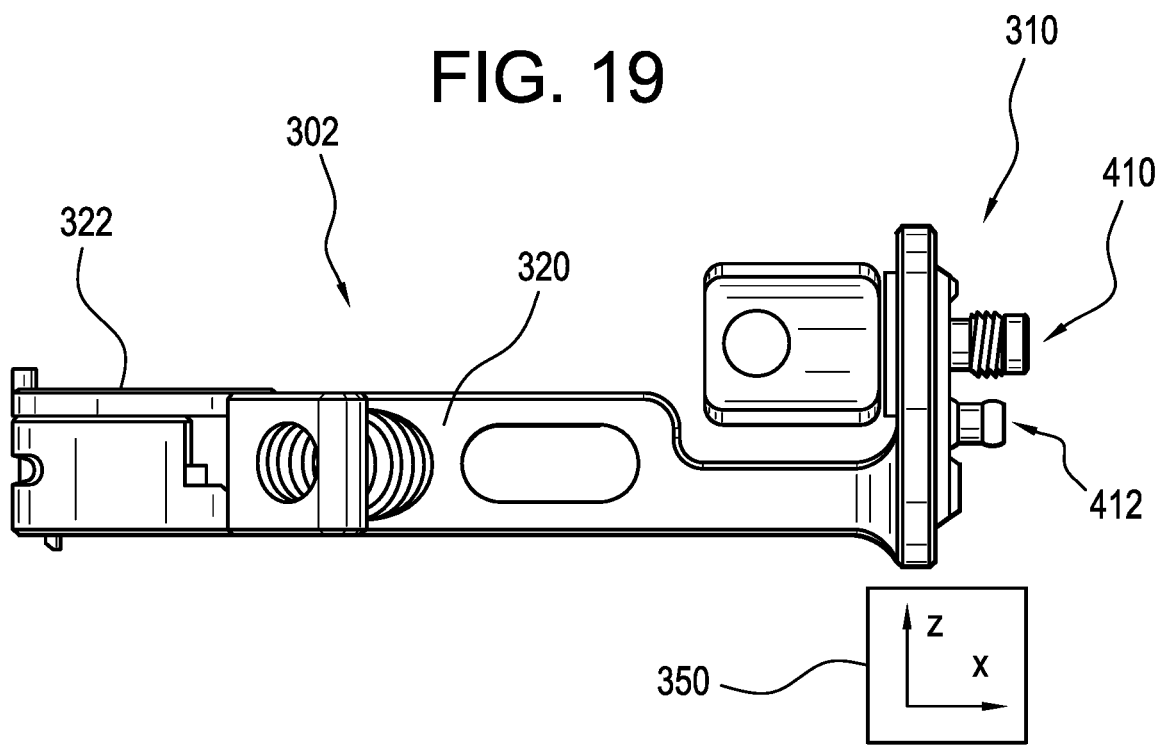
FIG. 19 is a side view of the instrument adapter of FIG. 18.

The first coupling component 310 can be attached to or formed on a second end of the arm 320, where the second end is opposite the first end of the arm. FIG. 19 illustrates a side view of the instrument adapter 302. As can be seen in FIG. 19, the first component 310 can be integrally formed with the adapter 302. In other embodiments, the first component 310 can be welded, threaded, glued, or otherwise attached to the instrument adapter 302. The screw 410 and the pin 412 can extend parallel to a longitudinal axis of the arm 320 of the instrument adapter 302. In other words, the screw 410, the pin 412, and the arm 320 can each extend parallel to and along the X-axis. In other embodiments, the instrument adapter 302 can have a different geometric configuration such that the instrument arm 320 can extend at an oblique angle relative to the screw 410 and the pin 412.

Figure 20:
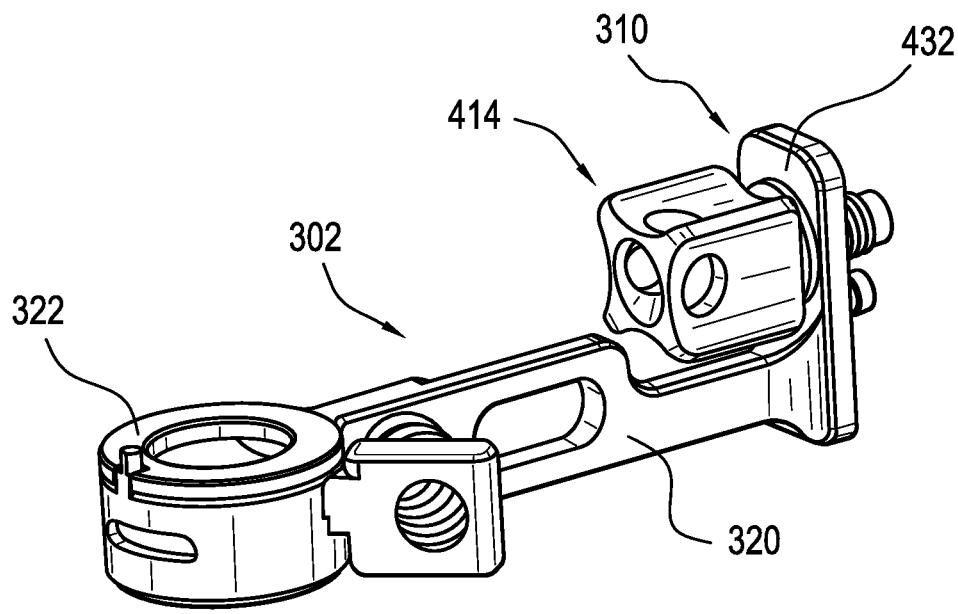
FIG. 20 is an alternative perspective view of the instrument adapter of FIG. 18.
Figure 21:
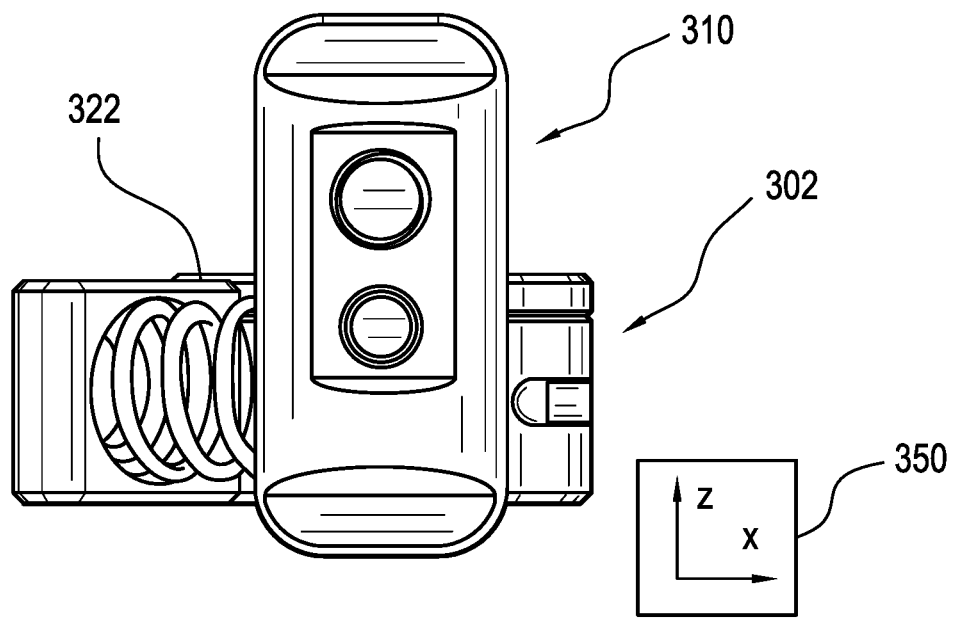
FIG. 21 is a front view of the instrument adapter of FIG. 18.

FIG. 20 illustrates the instrument adapter 302 with the first component 310 in a perspective view, with the back surface 432 of the first component 310 visible. FIG. 21 shows the instrument adapter 302 with a front view of the first component 310 (i.e., a view showing a ZY plane, with the X-axis extending into the page). As shown, a longitudinal axis of the first cylindrical surface 404 (i.e., the Z-axis) can be disposed perpendicular to a longitudinal axis of the adapter arm 320, which extends into the page in the view of FIG. 21. In other embodiments, the first component 310 can be disposed in a different positional relationship with respect to the adapter arm 320, and, more broadly, to the instrument adapter 302 and/or an instrument disposed therein.

FIGS. 22-26 illustrate an embodiment of a method of using the coupling 308 to attach a first object to a second object, e.g., an instrument to a navigation array. Except as indicated below, the steps of the described method can be performed in various sequences, and one or more steps can be omitted or added. Additionally, the instruments illustrated in the drawings are merely examples and alternative embodiments of the instruments, e.g., different first and/or second objects, etc., can be used in conjunction with the steps described below. A detailed description of every sequence of steps is omitted here for the sake of brevity.

In use, the first component 310 and the second component 312 can be coupled to one another to lock all degrees of freedom between the first object (e.g., an instrument adapter 302) and the second object (e.g., the navigation array 304) and to position the first object and the second object in a known and fixed relative position and orientation. As will be described in detail below, the first component 310 can be aligned with the second component 312. The first component 310 can then be brought into contact with the second component 312 such that the first component 310 is seated or placed against the second component 312. The first component 310 and the second component 312 can then be mated or secured to complete the coupling of the first object to the second object.

Figure 22:
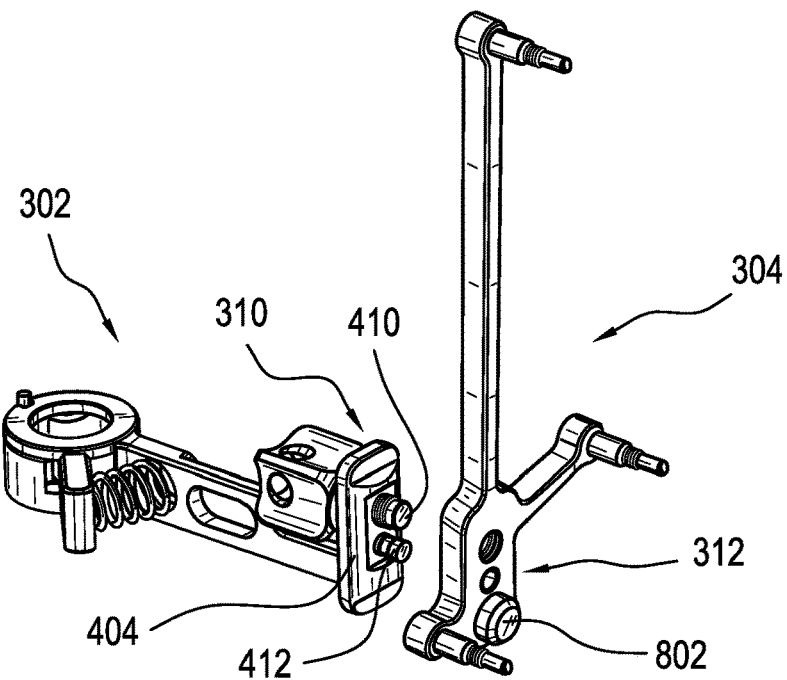
FIG. 22 is a perspective view of the system of FIG. 3 with the first object associated with the first coupling component aligned with the second object associated with the second coupling component.
Figure 23:
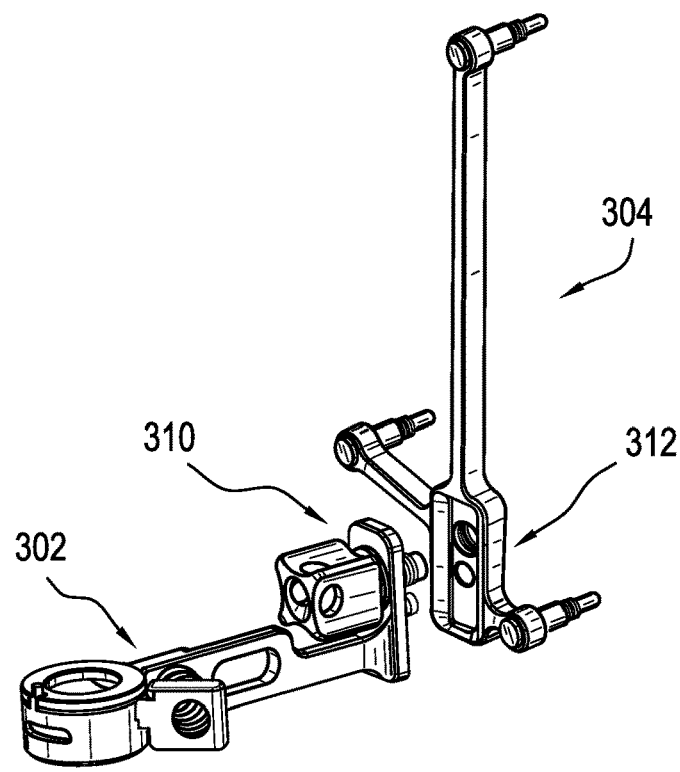
FIG. 23 is an alternative perspective view of the system of FIG. 3 with the first object associated with the first coupling component aligned with the second object associated with the second coupling component.

As shown in FIGS. 22 and 23, the first component 310 can be aligned with the second component 312. More particularly, the screw 410 extending from the first coupling component 310 can be aligned with the first opening 514 of the second component 312. The pin 412 extending from the first component 310 can be aligned with the second opening 516 of the second component 312. Proper orientation of the second object 304 and, more particularly, of the second coupling component 312 can be visually confirmed, for example, by confirming that the identification pin 802 is visible on a lower portion of the back surface 520 of the second component 312.

Figure 24:
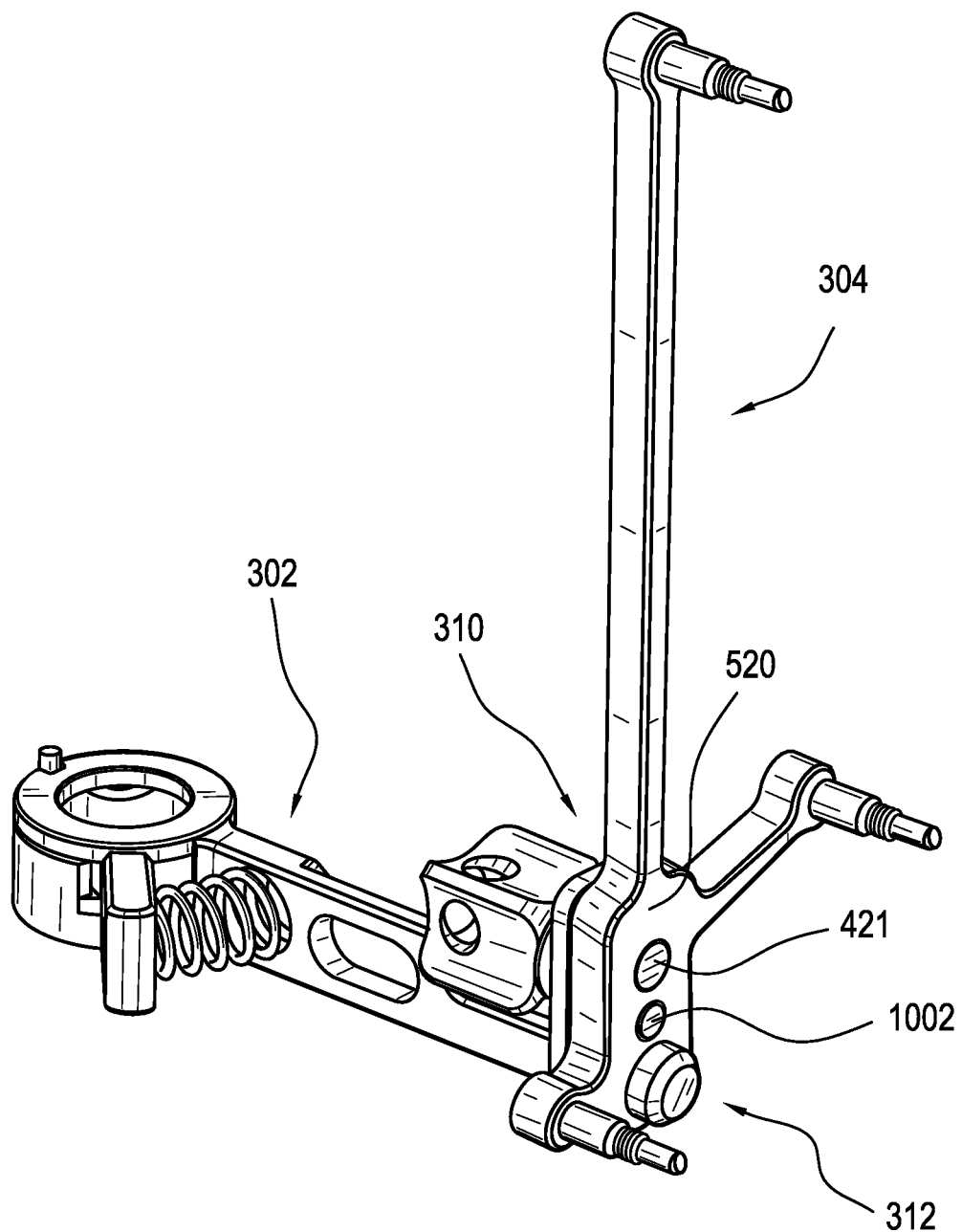
FIG. 24 is a perspective view of the system of FIG. 3 with the first coupling component associated with the first object seated within the second coupling component associated with the second object.
Figure 25:
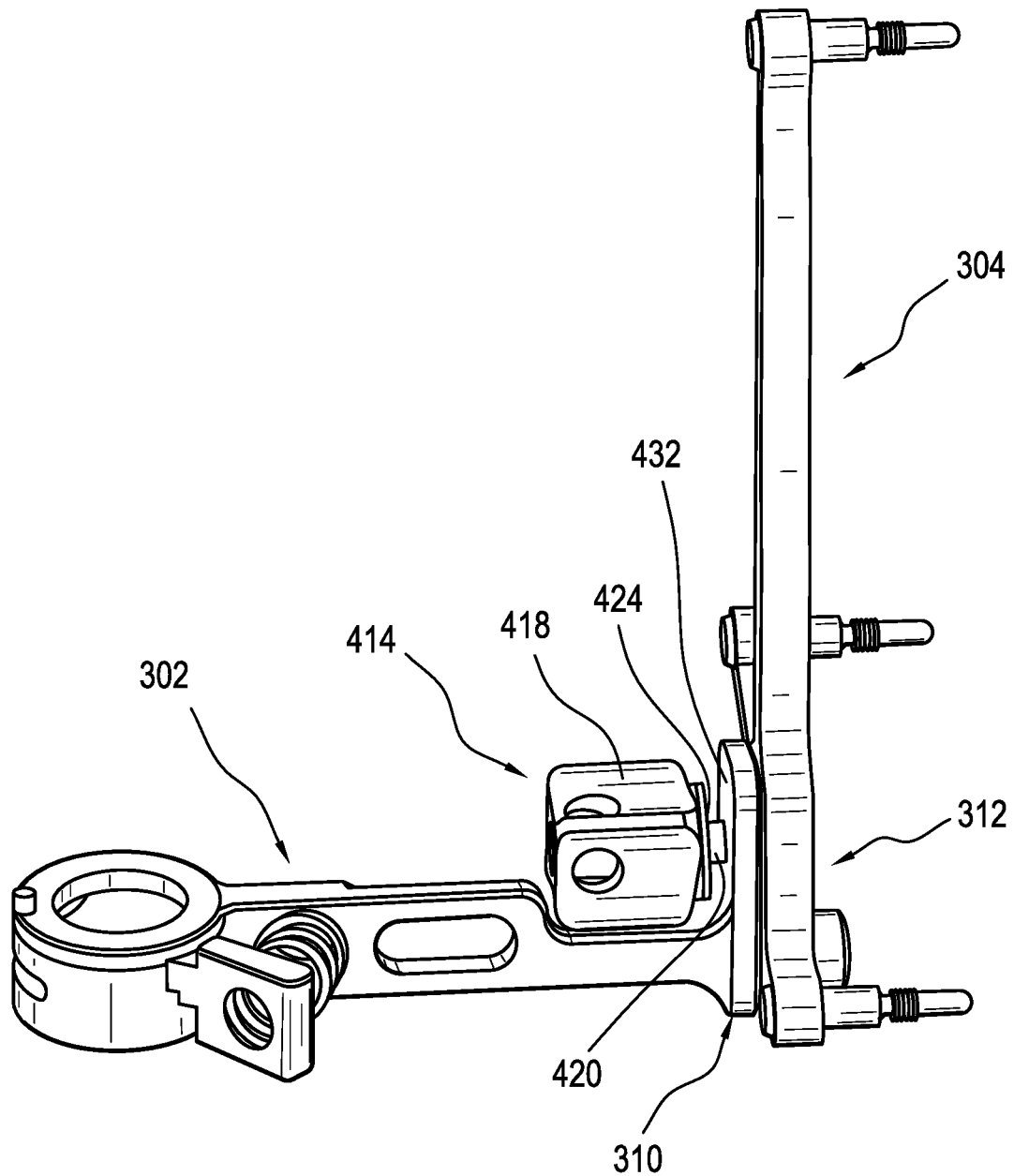
FIG. 25 is a side view of the system of FIG. 3 with the first coupling component associated with the first object seated within the second coupling component associated with the second object.
Figure 26:
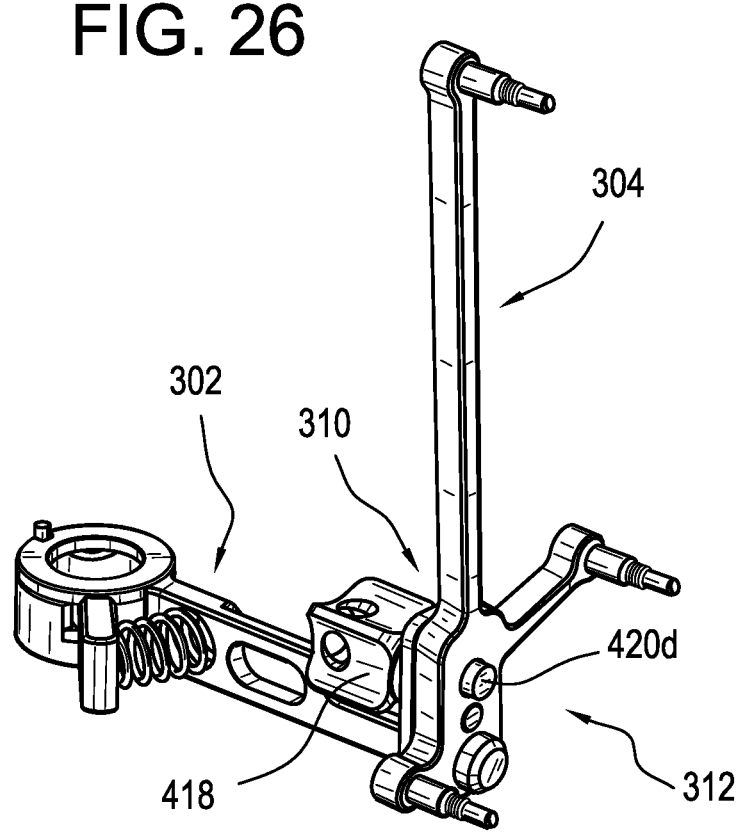
FIG. 26 is a perspective view of the system of FIG. 3 with the first coupling component associated with the first object secured to the second coupling component associated with the second object.
Figure 27:
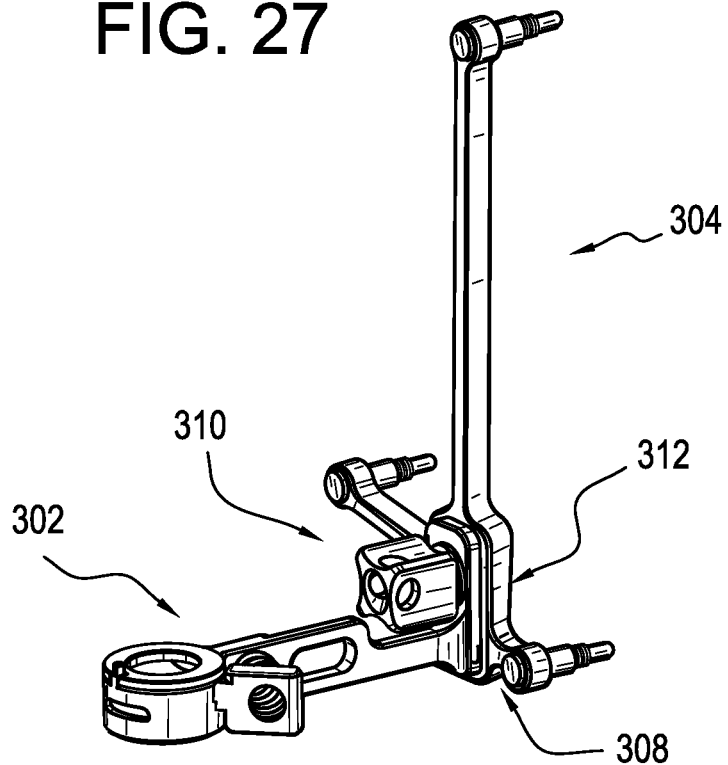
FIG. 27 is an alternative perspective view of the system of FIG. 3 with the first coupling component associated with the first object secured to the second coupling component associated with the second object.
Figure 28:
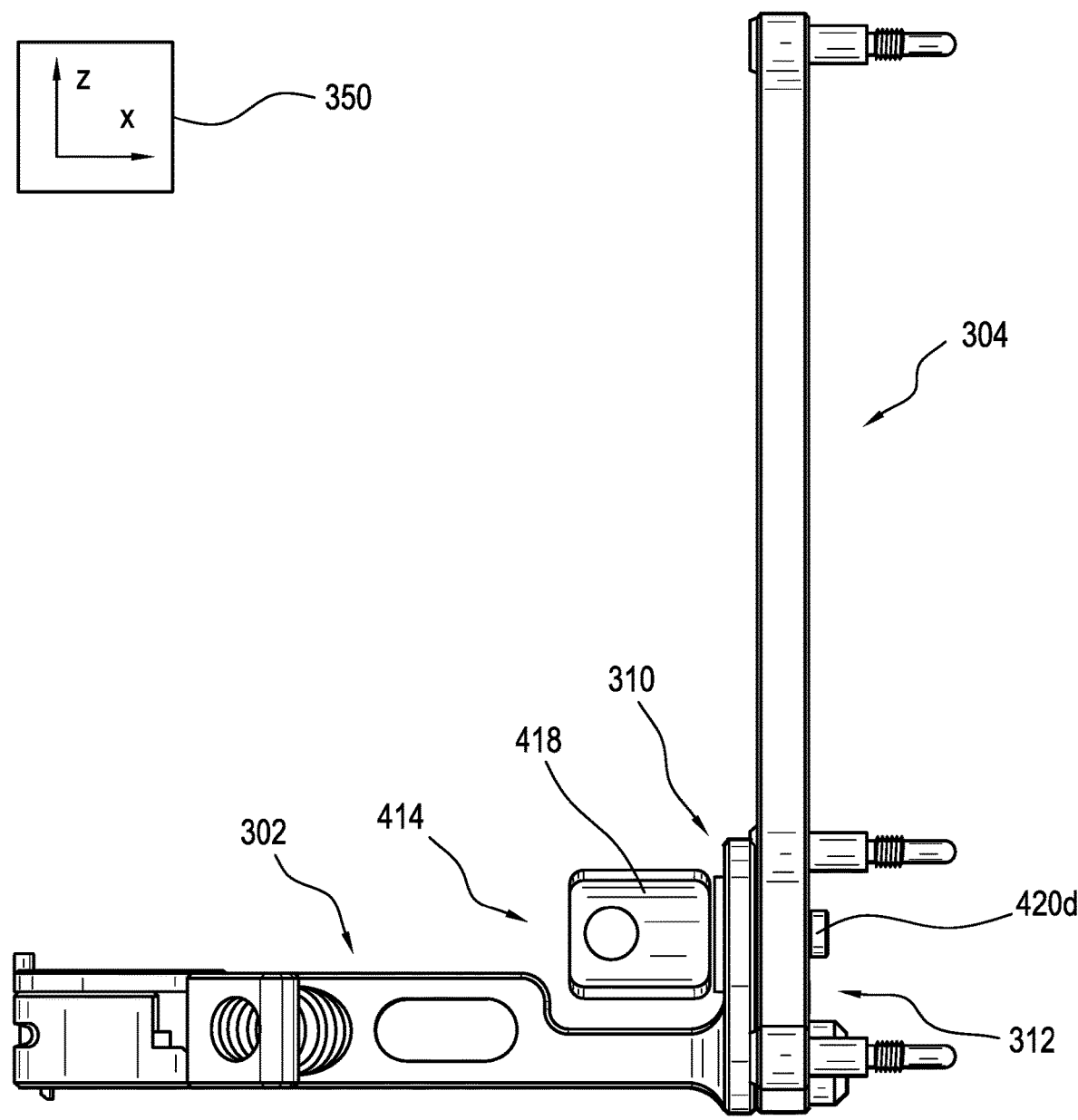
FIG. 28 is a side view of the system of FIG. 3 with the first coupling component associated with the first object secured to the second coupling component associated with the second object.

Next, the first component 310 and the second component 312 can be moved together such that the cylindrical surface 404 of the first coupling component 310 can be placed or seated against the prismatic surface 502 of the second coupling component 312. FIGS. 24 and 25 illustrate the first component 310 seated against the second component 312. The screw 410 can be received within the first opening 514 and the pin 412 can be received within the second opening 516. As described above in greater detail with reference to FIG. 14, in the seated configuration, the distal surface 1002 of the pin 412 and the distal surface 421 of the screw 410 can be flush with the back surface 520 of the second component 312. In some embodiments, this can evidence that the first threaded portion 422 of the screw 410 is not fully threadably engaged with the first opening 514. As can be seen in FIG. 25, the screw assembly 414 and, more particularly, the planar surface 424 of the handle 418 can be a distance away from the back surface 432 of the first component 310. A portion of the screw post 420 can extend proximally from the back surface 432 of the first component 310 between the handle 418 and the back surface. In some such embodiments, with the first component 310 seated against the second component 312, the planar surface 424 of the handle 418 can be parallel to but removed from the back surface 432 of the first component.

Once the first component 310 is placed against the second component 312, a force can be applied to couple the first component 310 with the second component 312. In some embodiments, the handle 418 can be rotated in the first direction to drive the screw 410 in the first direction. Rotating the screw 410 in the first direction can move the screw distally through the first opening 514. The threaded portion 422 of the screw 410 can threadably engage with the threaded inner surface 518 of the first opening 514. Driving the screw 410 can mate the first component 310 to the second component 312, thereby securing the first component 310 against the second component 312. In some embodiments, the handle 418 can be rotated in the first direction until the planar surface 424 abuts the back surface 432 of the first component 310. More particularly, driving the screw 410 can pull and lock the cylindrical surface 404 securely against the prismatic surface 502 of the second coupling component 312. As discussed above, in some instances securing the first component 310 and the second component 312 can result in a perfectly aligned configuration of the first and second components 310, 312, while, in other instances, the first component 310 and the second component 312 may be secured in an imperfect alignment. Regardless, after securing the coupling 308, the first component 310 and the second component 312 can be in a known position and orientation with negligible play or relative movement therebetween.

In some embodiments, relative movement between the first component 310 and the second component 312 can be restricted in all six degrees of freedom when an entire length of the threaded portion 422 (i.e., from the proximal end 422p of the threaded portion to the distal end 422d of the threaded portion) is engaged with corresponding threads of the threaded inner surface 518 of the first opening 514. A length of the threaded portion 422 of the screw 410 can be selected to achieve various functions during coupling. For example, the length can be selected such that the distal end 422d of the threaded portion 422 engages threads of the threaded inner surface 518 of the first opening 514 when the first coupling component 310 is seated within the second coupling component 312. In such arrangements, engagement of the threads can provide mechanical advantage to help draw the coupling components 310, 312 together during coupling and to urge the coupling components apart during decoupling.

FIGS. 26-30 show various views of the navigation array 304 coupled to the instrument adaptor 302 with the coupling 308 in the fully mated or secured position. The unthreaded distal end 420d of the screw 410 can extend beyond the back surface 520 of the second component 312. In some embodiments, this can serve as a visual confirmation that the first component 310 and the second component 312 have been coupled such that relative movement between the two components is sufficiently blocked or restricted. The planar surface 424 of the screw assembly 414 can bear against the back surface 432 of the first component 310 to press the first component 310 into the second component 312.

As discussed in detail above, rotating the screw 410 can engage the threaded inner surface 518 of the first opening 514 of the second coupling 312, and can block relative motion between the first component 310 and the second component 312 along and about the X-axis and the Y-axis. Relative rotation about the Z-axis can also be blocked. To the extent that relative movement between the first component 310 and the second component 312 exists due to frictional forces once the screw 410 has engaged with the threaded surface 518 of the first opening 514, the pin 412 received within the second opening 516 can further limit such relative motion along the Z-axis, as described above.

Moreover, the first component 310 and the second component 312 can be coupled in a known position and/or orientation such that the associated first object (e.g., the instrument adapter 302) and the associated second object (e.g., the navigation array 304) exist in a known position and/or orientation relative to one another. As such, the navigation array 304 can be used with the navigation system 307 to accurately and precisely locate and navigate the instrument adapter 302 and/or the instrument 306 disposed therein. While the description provided for herein discusses an instrument adapter 302 associated with a component of the coupling 308, an instrument can be directly associated with a component of the coupling 308 without the use of an instrument adapter. In other words, a first component 310 or a second component 312 of the coupling 308 can be attached to or otherwise disposed on an instrument. In this manner, the instrument can be directly coupled to a navigation array 304 (or other object) using the coupling 308.

Decoupling the first component 310 from the second component 312 can be achieved by disengaging the screw 410 from the threaded inner surface 518 of the first opening 514. In some embodiments, this can include rotating the handle 418 in the second direction to rotate the screw 410 in the second direction. More particularly, as the screw 410 is rotated in the second direction, the threaded portion 422 of the screw 410 can move proximally through the opening 514 such that a proximal end of the threaded portion 422 can exit the threaded surface 518 of the first opening 514. The first component 310 and the second component 312 can be completely decoupled when the distal end 422*d* of the threaded portion exits the threaded surface 518 of the first opening 514. The first component 310 can then be moved away from the second component 312. In some embodiments, decoupling the first component 310 and the second component 312 can include inserting an instrument through one or more of the openings 430 in the handle 418 of the screw assembly 414 and rotating the instrument thereby increasing the torque applied to the handle 418.

Figure 31:
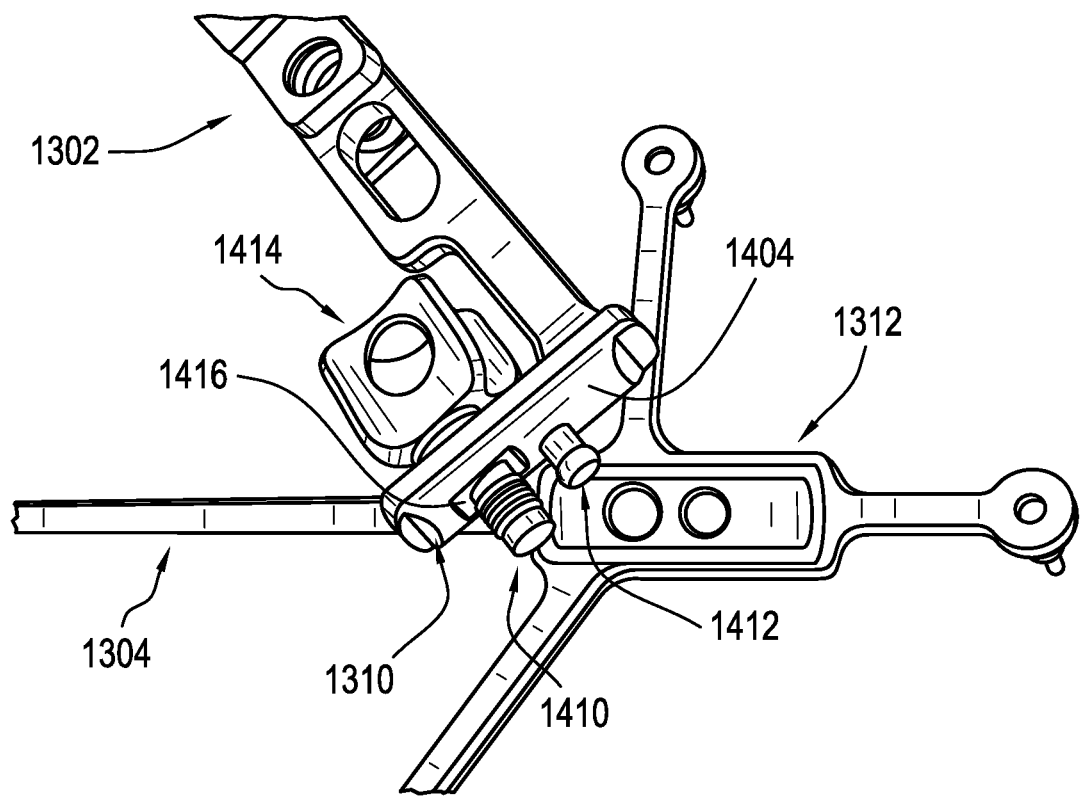
FIG. 31 shows an alternative embodiment of a coupling according to the present disclosure.
Figure 32:
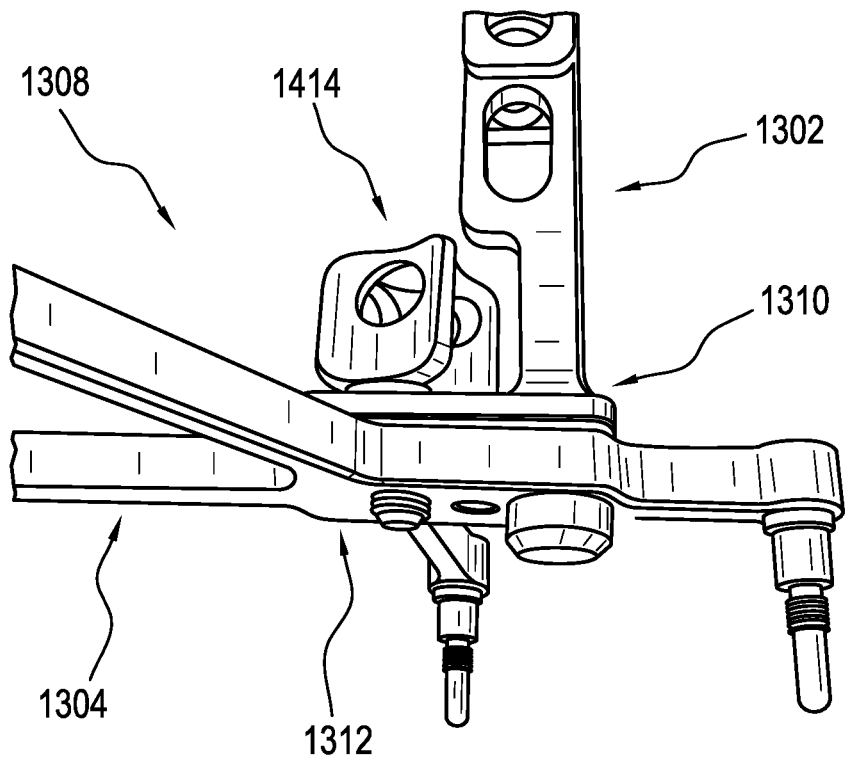
FIG. 32 shows the coupling of FIG. 31 in a mated configuration.
Figure 33:
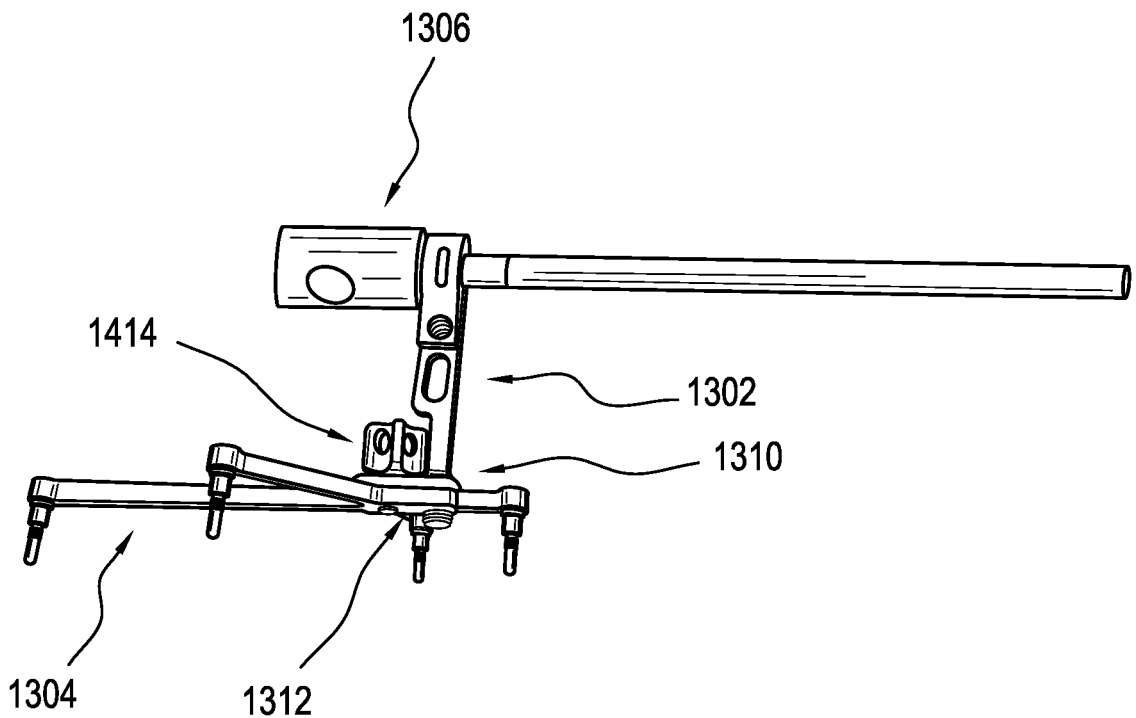
FIG. 33 shows the coupling of FIG. 31 in a mated configuration with a first object associated with a first coupling component and a second object associated with a second coupling component.

FIGS. 31-33 illustrate an alternative embodiment of a coupling 1308. Except as indicated below, the structure, operation, and use of this embodiment is similar or identical to that of the coupling 308 described above. Accordingly, a detailed description of said structure, operation, and use is omitted here for the sake of brevity.

The coupling 1308 can include a first component 1310 associated with a first object (e.g., an instrument adapter 1302) and a second component 1312 associated with a second object (e.g., a navigation array 1304). With reference to FIG. 31, the first coupling component 1310 can include a cylindrical surface 1404, a screw 1410, and a pin 1412. The screw 1410 can extend from a planar inlay 1416 of the cylindrical surface 1404. The planar inlay 1416 can be configured such that it spans only a region of the cylindrical surface that surrounds the screw 1410 extending therefrom. As such, the pin 1410 can extend from a convex portion of the cylindrical surface 1404.

FIGS. 32 and 33 show the first object (e.g., instrument adapter 1302) coupled to the second object (e.g., navigation array 1304) by the coupling 1308. In similar manner as to the coupling 308, described above, the first component 1310 can be coupled to the second component 1312 to restrict relative motion in all six degrees of freedom such that there is negligible play between the first component 1310 and the second component 1312. Accordingly, the instrument adapter 1302 and the navigation array 1304 can be coupled in a known orientation by the coupling 1308. An instrument 1306 can be received within the instrument adapter 1302 such that the position of the instrument 1306 can be accurately and precisely tracked using the navigation array 1304.

As evident from the foregoing, in at least some embodiments, the systems and methods disclosed herein can provide a coupling with a fully defined interface for coupling an instrument and/or an instrument adapter and a navigation array with minimal play and unique orientation for accurate and precise navigation of surgical instruments.

Although specific embodiments are described above, it should be understood that numerous changes may be made within the spirit and scope of the concepts described. Accordingly, it is intended that this disclosure not be limited to the described embodiments, but that it have the full scope defined by the language of the following claims. The above embodiments describe a coupling 308 that couples a navigation array to an instrument or an instrument adapter. While this is one contemplated use, the methods and devices of the present disclosure can be equally adapted for use with other objects. As such, the devices and components described herein can be formed in a variety of sizes and materials appropriate for use in various applications.

One skilled in the art will appreciate further features and advantages based on the above-described embodiments. Accordingly, the disclosure is not to be limited by what has been particularly shown and described. All publications and references cited herein are expressly incorporated herein by reference in their entirety.

The invention claimed is:

1. A coupling for attaching a first object and a second object, the coupling comprising:
   a first coupling component associated with the first object, the first coupling component having a cylindrical surface extending longitudinally along a first axis, as well as a screw and a pin extending from a planar surface inlayed in the cylindrical surface longitudinally along a second axis that is transverse to the first axis; and
   a second coupling component associated with the second object, the second coupling component having a prismatic surface, a first opening configured to receive the screw, and a second opening configured to receive the pin;
   wherein the first coupling component and the second coupling component are adapted to mate with one another such that the cylindrical surface is seated against the prismatic surface and relative motion between the first coupling component and the second coupling component is restricted in all six degrees of freedom.

2. The coupling of claim 1, wherein the pin includes a proximal end, a distal end, and a reduced diameter portion located proximal to the distal end of the pin.

3. The coupling of claim 2, wherein the distal end of the pin is a sphere shape.

4. The coupling of claim 2, wherein the first coupling component and the second coupling component are configured such that, when the first coupling component and the second coupling component are mated, at least a portion of the reduced diameter portion of the pin is disposed within the second opening of the second coupling component.

5. The coupling of claim 4, wherein the pin is configured to limit relative movement between the first coupling component and the second coupling component along a longitudinal axis of the cylindrical surface.

6. The coupling of claim 2, wherein the first component and the second component are configured such that a clearance exists between the pin and an inner surface of the second opening when the pin of the first component is received within the second opening of the second component.

7. The coupling of claim 6, wherein the first component and the second component are configured such that the distal end of the pin can contact the inner surface of the second opening to restrict movement of the second coupling component relative to the first coupling component.

8. The coupling of claim 1, wherein the first coupling component and the second coupling component are adapted to mate with one another such that a first line of contact and a second line of contact extend between the first coupling component and the second coupling component.

9. The coupling of claim 8, wherein the first line of contact and the second line of contact extend between the cylindrical surface of the first coupling component and the prismatic surface of the second coupling component.

10. The coupling of claim 8, wherein the first line of contact and the second line of contact extend along substantially an entire length of the cylindrical surface.

11. The coupling of claim 10, wherein the first line of contact and the second line of contact are located on opposite sides of a midline of the cylindrical surface.

12. The coupling of claim 8, wherein the prismatic surface includes a first end and a second end with a first sidewall and a second sidewall extending therebetween, the first sidewall and the second sidewall extending at an angle relative to a backstop of the prismatic surface.

13. The coupling of claim 12, wherein the first line of contact extends along the first sidewall of the prismatic surface and the second line of contact extends along the second sidewall of the prismatic surface.

14. The coupling of claim 1, wherein the first object is a surgical instrument and the second object is a navigation array.

15. The coupling of claim 1, wherein the screw includes a post having a proximal end, a distal end, and a threaded portion located proximal to the distal end of the screw.

16. The coupling of claim 1, wherein the first coupling component includes a back surface opposite the cylindrical surface, wherein the back surface of the first coupling component is a flat planar surface.

17. The coupling of claim 16, wherein the first coupling component includes a through-hole configured to receive the screw such that the screw extends through the first coupling component perpendicular to the back surface of the first coupling component.

18. A method of coupling a first object and a second object, the method comprising:
aligning a first coupling component associated with the first object and a second coupling component associated with the second object, the first coupling component having a cylindrical surface extending longitudinally along a first axis, as well as a screw and a pin extending from a planar surface inlayed in the cylindrical surface longitudinally along a second axis that is transverse to the first axis, and the second coupling component having a prismatic surface, a first opening, and a second opening;
advancing the first coupling component with respect to the second component such that the cylindrical surface is seated against the prismatic surface, the screw is received within the first opening, and the pin is received within the second opening; and
securing the first component and the second component such that relative movement between the first component and the second component is restricted in six degrees of freedom.

19. The method of claim 18, further comprising limiting relative movement between the first component and the second component by contact between the pin and an inner surface of the second opening.

20. The method of claim 18, wherein securing the first component and the second component further comprises driving the screw within the first opening.

21. The method of claim 20, wherein driving the screw prevents relative movement between the first component and the second component in at least five degrees of freedom.

22. The method of claim 20, wherein the pin restricts relative movement between the first component and the second component after driving the screw to mate the first component and the second component.

23. The method of claim 22, wherein the pin contacts an inner surface of the second opening and restricts relative movement between the first component and the second component.

24. The method of claim 22, wherein the restricted relative movement between the first component and the second component is along a longitudinal axis of the cylindrical surface.

25. The method of claim 20, wherein driving the screw to mate the first component and the second component further comprises rotating the screw in a first direction such that a threaded portion of the screw fully engages with a threaded inner surface of the first opening.

26. The method of claim 25, wherein an unthreaded distal end of the screw extends beyond a back surface of the second component when the screw fully engages with the threaded inner surface of the first opening.

27. The method of claim 20, wherein driving the screw includes rotating a handle of a screw assembly in a first direction until a planar surface of the handle abuts a back surface of the first component.

28. The method of claim 18, wherein the first component and the second component contact one another along a first line of contact and a second line of contact extending between the cylindrical surface of the first component and the prismatic surface of the second component.

29. The method of claim 28, wherein the first line of contact and the second line of contact are located on opposite sides of a midline of the cylindrical surface.

30. A coupling for attaching a first object and a second object, the coupling comprising:
a first coupling component associated with the first object, the first coupling component having an outer cylindrical surface with an inlayed planar surface, as well as a screw and a pin extending from the planar surface; and
a second coupling component associated with the second object, the second coupling component having a prismatic surface, a first opening configured to receive the screw, and a second opening configured to receive the pin;
wherein the first coupling component and the second coupling component are adapted to mate with one another such that the outer cylindrical surface of the first coupling component contacts the prismatic surface of the second coupling component and relative motion between the first coupling component and the second coupling component is restricted in all six degrees of freedom.

\* \* \* \* \*